(12) United States Patent
Ito et al.

(10) Patent No.: US 8,431,378 B2
(45) Date of Patent: Apr. 30, 2013

(54) AMINOTRANSFERASE, GENE ENCODING THE SAME, AND METHODS OF USING THEM

(75) Inventors: Noriyuki Ito, Takasago (JP); Yoshihiko Yasohara, Takasago (JP)

(73) Assignee: Kaneka Corporation, Osaka-shi (JP)

( * ) Notice: Subject to any disclaimer, the term of this patent is extended or adjusted under 35 U.S.C. 154(b) by 0 days.

(21) Appl. No.: 13/360,196

(22) Filed: Jan. 27, 2012

(65) Prior Publication Data

US 2012/0164724 A1 Jun. 28, 2012

Related U.S. Application Data

(62) Division of application No. 11/920,842, filed as application No. PCT/JP2006/310170 on May 22, 2006, now Pat. No. 8,133,705.

(30) Foreign Application Priority Data

May 23, 2005 (JP) ................................. 2005-149900

(51) Int. Cl.
| | |
|---|---|
| C12P 13/00 | (2006.01) |
| C12N 9/00 | (2006.01) |
| C12N 9/10 | (2006.01) |
| C12N 1/20 | (2006.01) |
| C12N 15/00 | (2006.01) |
| C07H 21/04 | (2006.01) |

(52) U.S. Cl.
USPC ........ 435/193; 435/128; 435/183; 435/252.3; 435/320.1

(58) Field of Classification Search ........................ None
See application file for complete search history.

(56) References Cited

U.S. PATENT DOCUMENTS

| 6,221,638 B1 | 4/2001 | Yamada et al. |
| 6,346,402 B1 | 2/2002 | Iwasaki et al. |
| 2002/0192786 A1 | 12/2002 | Yamada et al. |

FOREIGN PATENT DOCUMENTS

| EP | 0 404 146 A2 | 12/1990 |
| JP | 6-178685 A | 6/1994 |
| JP | 2846074 B2 | 10/1998 |
| JP | 2002-142793 A | 5/2002 |
| WO | WO 97/15682 A1 | 5/1997 |
| WO | WO 98/48030 A1 | 10/1998 |
| WO | WO 00/26351 A1 | 5/2000 |
| WO | WO 02/077183 A2 | 10/2002 |
| WO | WO0277183 | * 10/2002 |

OTHER PUBLICATIONS

Accession ABU19473, Jun. 19, 2003.*
Chica et al. Curr Opin Biotechnol. Aug. 2005;16(4):378-84.*
Sen et al. Appl Biochem Biotechnol. Dec. 2007;143(3):212-23.*
Accession Q4KBQ9. Published Aug. 2, 2005.
Ayonaha K. et al., gamma-Aminobutyrate: alpha-ketoglutarate aminotransferase from *Pseudomonas* sp. F-126: purification, crystallization, and enzymologic properties., Arch. Biochem.Biophys., 1980. vol. 200, No. 1, pp. 156 to 164.
Holden et al., Proceedings of the National Academy of Sciences of USA, National Academy of Science, Washington, DC, vol. 101, No. 39, pp. 14240-14245, Sep. 28, 2004, XP002399894.
International Preliminary Report on Patentability corresponding to PCT International Application No. PCT/JP2006/310170, mailed Dec. 6, 2007.
J.-S. Shin et al., Appl. Microbiol. Biotechnol. (2003) 61:463-471.
J.-S. Shin et al., J. Org. Chem. 2002, 67, 2848-2853.
US Notice of Allowance dated Nov. 15, 2011 issued in corresponding U.S. Appl. No. 11/920,842.
US Office Action dated Feb. 15, 2011 issued in corresponding U.S. Appl. No. 11/920,842.
US Office Action dated Nov. 1, 2010 issued in corresponding U.S. Appl. No. 11/920,842.

* cited by examiner

*Primary Examiner* — Christian Fronda
(74) *Attorney, Agent, or Firm* — Birch, Stewart, Kolasch & Birch, LLP.

(57) ABSTRACT

The invention relates to a novel aminotransferase, DNA encoding the enzyme, a recombinant vector into which the DNA has been introduced, and a transformant into which the vector has been introduced. Further, the invention also relates to a method for producing an optically active amino compound utilizing the enzyme or transformant. The aminotransferase of the invention has an ability of efficiently converting a ketone compound, particularly a cyclic ketone compound to an optically active amino compound. According to the invention, a method for efficiently producing an optically active amino compound, particularly an optically active cyclic amino compound is provided.

12 Claims, 1 Drawing Sheet

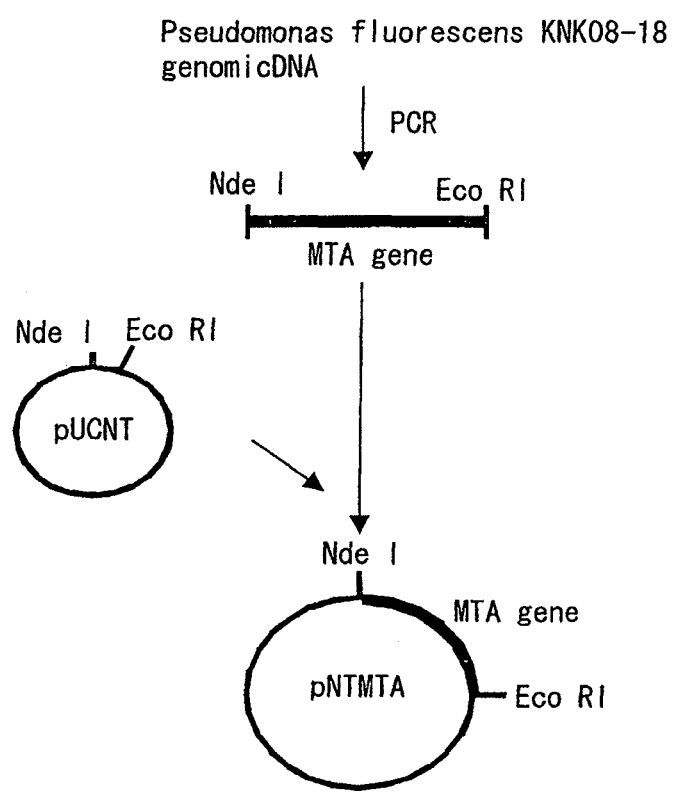

AMINOTRANSFERASE, GENE ENCODING THE SAME, AND METHODS OF USING THEM

This application is a Divisional of application Ser. No. 11/920,842, filed on Nov. 21, 2007 now U.S. Pat. No. 8,133,705. Application Ser. No. 11/920,842 is the National Phase of PCT International Application No. PCT/JP2006/310170 filed on May 22, 2006, and claims priority under 35 U.S.C. §119(a) to Patent Application No. 2005-149900 filed in Japan on May 23, 2005, all of which are hereby expressly incorporated by reference into the present application.

TECHNICAL FIELD

The present invention relates to an enzyme capable of converting a ketone compound to an optically active amino compound efficiently via amino group transferring reaction, and a method of producing the optically active amino compound by using the enzyme. The optically active amino compound obtained by the present invention can be used as an intermediate for medical drugs, agricultural chemicals, and the like.

BACKGROUND ART

As one conventional example of producing an optically active amino compound via an amino group transferring reaction, it has been reported that amino group transfer to benzylacetone, phenylacetone, and acetophenone by using ω-amino acid transaminase obtained from *bacillus megaterium* can synthesize optically active amino compounds from these ketones, respectively (U.S. Pat. No. 2,846,074: Patent Citation 1). However, this synthesis is not so industrially applicable due to extremely low substrate concentration in its reaction solution.

Meanwhile, WO00/26351 (Patent Citation 2) describes that an aryl alkyl ketone such as 3-hydroxy acetophenone, 3-trifluoromethylphenylacetone, or the like is reacted with (S)-phenethylamine: pyruvate transaminase, thereby to synthesize an optically active amino compound of the ketone compound. Patent Citation 2, however, does not refer to cyclic ketones.

Japanese Patent Application Publication No. 2002-142793 (Patent Citation 3) obtains an aminotransferase from *bacillus* sp. The aminotransferase is characterized in that it will not be inhibited by gabaculine, which is an enzyme inhibitor. Patent Citation 3 describes that it is possible to synthesize an optically active amino compound from propiophenone by transferring an amino group in n-butylamine thereto by using the aminotransferase. However, this synthesis is not so industrially applicable due to extremely low substrate concentration in its reaction solution.

[Patent Citation 1] Patent No. 2846074
[Patent Citation 2] WO 00/26351
[Patent Citation 3] Japanese Patent Application Publication, Tokukai, No. 2002-142793

DISCLOSURE OF INVENTION

[Technical Problem]
An object of the present invention is to provide a method of efficiently producing an optically active amino compound from a ketone compound, especially cyclic ketone compound. Such an optically active amino compound is useful as an intermediates for medical drugs, agricultural agents, etc.

[Technical Solution]
The inventors of the present invention found a microorganism having a high activity to cyclic ketones and an amino group transfer activity with stereo-selectivity, as a result of screening of various microorganisms form soils. Moreover, the inventors of the present invention successfully isolated and purified an enzyme having the activity from the microorganism. Furthermore, as a result of detailed studies on the reactivity properties of the aminotransferase, the inventors of the present invention found that the enzyme has such an excellent property that if (S)-α-phenethylamine or the like is used as an amino donor, the enzyme is highly active not only with the cyclic ketones, but also with ketone compounds of wide variety such as arylalkylketone such as benzylacetone, and pyruvic acid, so as to produce an optically active amino compound corresponding to the ketone compound. Furthermore, via gene recombination technique, the inventors of the present invention obtained a gene encoding the enzyme, and found a base sequence thereof. Furthermore, the inventors of the present invention bred, from the gene, a transformant producing the enzyme. As a result, the inventors of the present invention prepared a transformant having a higher activity, and thereby established a method of industrially producing an optically active amino compound.

That is, the present invention is an aminotransferase having physical and chemical properties (1) to (3):

(1) effect: the aminotransferase catalyzes an amino group transfer reaction that produces acetophenone and 1-benzyl-3-aminopyrrolidine from 1-benzyl-3-pyrrolidinone and optically active (S)-α-phenethylamine;

(2) substrate specificity:
 (a) amino donor: the aminotransferase is active with (S)-α-phenethylamine, but substantially inactive with 3-alanine, taurine, putrescine, DL-ornithine, and DL-lysine; and
 (b) amino acceptor: the aminotransferase is active with pyruvic acid and glyoxylic acid, and (3) molecular weight: approximately 120,000 when measured by gel filtration, and approximately 53,000 when measured by SDS-polyacrylamide gel electrophoresis.

Moreover, the present invention is an aminotransferase having the amino acid sequence of SEQ ID NO:1 in the sequence list, or an aminotransferase having an amino acid sequence of SEQ ID NO:1 in the sequence list, in which one or some amino acids are deleted, replaced, inserted, or added in the amino acid sequence of SEQ ID NO:1 in the sequence list, and producing acetophenone and 1-benzyl-3-aminopyrrolidine from 1-benzyl-3-pyrrolidinone and optically active (S)-α-phenethylamine.

Moreover, the present invention is DNA encoding the enzyme, a vector having the DNA, and a transformant obtained by transformation with a vector.

Moreover, the present invention is a method of producing an optically active amino compound, the method comprising:

reacting a carbonyl compound in the presence of an amino donor with the enzyme or a culture product of a microorganism capable of producing the enzyme, the carbonyl compound being represented by General Formula (1):

(1)

where P and Q are an substituted or unsubstituted alkyl group, branched alkyl group, aryl group, heteroaryl group, aryloxy group, heteroaryloxy group, alkoxy group, alkoxycarbonyl group, alkenyl group, alkynyl group, cycloalkyl group, aralkyl group, or hetero aralkyl group, and may form a ring by bonding with each other, but are different from each other in chirality, the optically active amino compound being represented by General Formula (2):

(2)

where P and Q are the same as in General Formula (1).

Moreover, the present invention is a method of producing an optically active amino compound, the method comprising:

reacting a carbonyl compound in the presence of an amino donor with the enzyme or a culture product of a microorganism capable of producing the enzyme, the carbonyl compound being represented by General Formula (3):

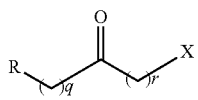

(3)

where q is an integer of 0 to 7, r is an integer of 0 to 2, R is a substituted or unsubstituted aryl group of carbon number of 6 to 14, heteroaryl group of carbon number of 4 to 14, aryloxy group of carbon number of 6 to 14, heteroaryloxy group of carbon number of 4 to 14, alkoxy group of carbon number of 1 to 5, alkoxycarbonyl group of carbon number of 2 to 5, branched alkyl group of carbon number of 3 to 5, alkenyl group of carbon number of 2 to 5, alkynyl group of carbon number of 2 to 5, cycloalkyl group of carbon number of 5 to 7, methyl group, or carboxyl group, X is a hydrogen atom or a substituted or unsubstituted methyl group, and $q \geq r$ if R is the methyl group, the optically active amino compound being represented by General Formula (4):

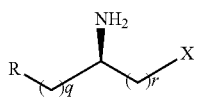

(4)

where q, r, R and X are the same as in General Formula (3).

Moreover, the present invention is a method of producing an optically active amino compound, the method comprising:

reacting an enantiomer mixture of an amino compound in the presence of an amino acceptor, or a culture product of a microorganism capable of producing the enzyme, the amino compound being represented by General Formula (5):

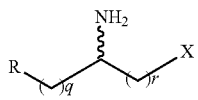

(5)

where q is an integer of 0 to 7, r is an integer of 0 to 2, R is a substituted or unsubstituted aryl group of carbon number of 6 to 14, heteroaryl group of carbon number of 4 to 14, aryloxy group of carbon number of 6 to 14, heteroaryloxy group of carbon number of 4 to 14, alkoxy group of carbon number of 1 to 5, alkoxycarbonyl group of carbon number of 2 to 5, branched alkyl group of carbon number of 3 to 5, alkenyl group of carbon number of 2 to 5, alkynyl group of carbon number of 2 to 5, cycloalkyl group of carbon number of 5 to 7, methyl group, or carboxyl group, X is a hydrogen atom or a substituted or unsubstituted methyl group, and $q \geq r$ if R is the methyl group, the optically active amino compound being represented by General Formula (6):

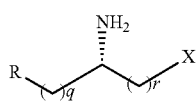

(6)

where q, r, R and X are the same as in General Formula (5).

Moreover, the present invention is a method of producing an optically active amino compound, the method comprising:

reacting a carbonyl compound in the presence of an amino donor with the enzyme, or a culture product of a microorganism capable of producing the enzyme, the carbonyl compound being represented by General Formula (7):

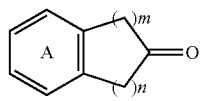

(7)

where m is an integer of 0 to 3, n is an integer of 2 to 4 (where n>m), and the ring A is a substituted or unsubstituted benzene ring, the optically active amino compound being represented by General Formula (8):

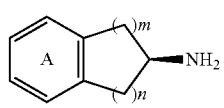

(8)

where m, n, and the ring A are the same as in General Formula (7).

Moreover, the present invention is a method of producing an optically active amino compound, the method comprising:

reacting an enantiomer mixture of an amino compound in the presence of an amino acceptor with the enzyme, or a culture product of a microorganism capable of producing the enzyme, the amino compound being represented by General Formula (9):

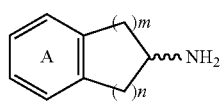

(9)

where m is an integer of 0 to 3, n is an integer of 2 to 4 (where n>m), and the ring A is a substituted or unsubstituted benzene ring, the optically active amino compound being represented by General Formula (10):

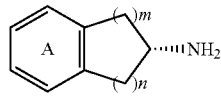

(10)

where m, n, and the ring A are the same as in General Formula (9).

Moreover, the present invention is a method of producing an optically active amino compound, the method comprising:

reacting a carbonyl compound in the presence of an amino donor with the enzyme, or a culture product of a microorganism capable of producing the enzyme, the carbonyl compound being represented by General Formula (11):

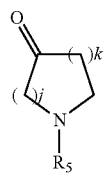

(11)

where j and k are independently an integer of 1 to 3 (where k≧j), $R_5$ is a hydrogen atom, aryl group of carbon number of 6 to 14, heteroaryl group of carbon number of 4 to 14, alkyl group of carbon number of 1 to 6, alkoxy group of carbon number of 1 to 6, acyl group of carbon number of 2 to 15, alkoxycarbonyl group of carbon number of 1 to 6, aralkyl group of carbon number of 7 to 15, aralkyloxycarbonyl group of carbon number of 8 to 16, or a sulfonyl group substituted with an alkyl group of carbon number of 1 to 6 or aryl group of carbon number of 6 to 14, the optically active amino compound being represented by General Formula (12):

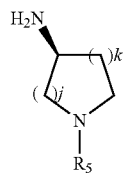

(12)

where j, k, and $R_5$ are the same as in General Formula (11).

Moreover, the present invention is a method of producing an optically active amino compound, the method comprising:

reacting an enantiomer mixture of an amino compound in the presence of an amino acceptor with the enzyme, or a culture product of a microorganism capable of producing the enzyme, the amino compound being represented by General Formula (13):

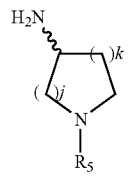

(13)

where j and k are independently an integer of 1 to 3 (where k≧j), $R_5$ is a hydrogen atom, aryl group of carbon number of 6 to 14, heteroaryl group of carbon number of 4 to 14, alkyl group of carbon number of 1 to 6, alkoxy group of carbon number of 1 to 6, acyl group of carbon number of 2 to 15, alkoxycarbonyl group of carbon number of 1 to 6, aralkyl group of carbon number of 7 to 15, aralkyloxycarbonyl group of carbon number of 8 to 16, or a sulfonyl group substituted with an alkyl group of carbon number of 1 to 6 or aryl group of carbon number of 6 to 14, the optically active amino compound being represented by General Formula (14):

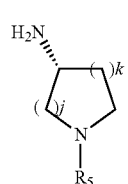

(14)

where j, k, and $R_5$ are the same as in General Formula (13).

[Effect of the Invention]

An enzyme having an activity to stereo-selectively transfer an amino group to a ketone compound, especially a cyclic ketone compound is isolated. A transformant with high productivity in producing the enzyme can be obtained. Further, the use of the transformant makes it possible to produce an optically active amino compound efficiently.

BRIEF DESCRIPTION OF DRAWINGS

FIG. 1 is a view illustrating how to construct a recombinant vector pNTMTA of the present invention.

BEST MODE FOR CARRYING OUT THE INVENTION

The present invention is descried below in details. Unless otherwise specified, DNA isolation, vector preparation, and genetic operations such as transformation can be carried out by methods described in literatures such as Molecular Cloning 2nd Edition (Cold Spring Harbor Laboratory Press, 1989), Current Protocols in Molecular Biology (Greene Publishing Associates and Wiley-Interscience), and the like.

An enzyme of the present invention has the following physical and chemical properties:

(1) Effect: it catalyzes an amino group transfer reaction that produces acetophenone and 1-benzyl-3-aminopyrrolidine from 1-benzyl-3-pyrrolidinone and optically active (S)-α-phenethylamine.

(2) Substrate Specificities:

(a) Amino donor: it is active with (s)-α-phenethylamine, but substantially inactive with β-alanine, taurine, putrescine, DL-ornithine and DL-lysine.

(b) Amino acceptor: it is active with pyruvic acid and glyoxylic acid.

(3) Molecular Weight: approximately 120,000 when measured by gel filtration, and approximately 53,000 when measured by SDS-polyacrylamide gel electrophoresis.

The following method is applicable to measure the activity of the amino group transferring reaction to produce acetophenone and 1-benzyl-3-aminopyrrolidine from 1-benzyl-3-pyrrolidinone and the optically active (S)-α-phenethylamine.

Into 0.9 mL of a substrate solution having the following composition, 0.1 mL of a purified enzyme solution adjusted to a protein concentration of 2 mg/mL is added. After carrying out reaction at 30° C. for 1 hour therein, 0.1 mL of 1N HCl is added therein to stop the reaction, thereby obtaining 1-benzyl-3-aminopyrrolidine, which is then quantitatively analyzed by high-performance liquid chromatography.

[Substrate Solution Composition]

| | |
|---|---|
| (S)-α-phenethylamine | 28.3 mM |
| 1-benzyl-3-pyrrolidinone | 28.3 mM |
| Pyridoxal phosphate | 0.02 mM |
| Potassium phosphate buffer (pH 7.0) | 0.1M |

[High-Performance Liquid Chromatography Analysis Conditions]

Column: Finepak SIL C18-T (JASCO Corp.)
Carrier: Distilled Water 1260 mL/Acetonitrile 740 mL/$KH_2PO_4$ 10 g/SDS 2.88 g (pH3.6)
Flow Rate: 1 mL/min
Detection: 254 nm
Column Temperature: 40° C.

The enzyme of the present invention is substantially inactive in the case where the amino donor is any of β-alanine, taurine, putrescine, DL-ornithine and DL-lysine. Here, the term "substantially inactive" means that amino group transfer activity measurement carried out in the following manner shows that the amino group transfer activity in the case where the amino donor is the amino compound is 1/100 or less, preferably 1/1000 or less, and further preferably 1/10000 or less of the amino group transfer activity in the case where the amino donor is (S)-α-phenethylamine.

The amino group transfer activity measurement is carried out as follows: Firstly, 20 μL of a purified enzyme solution having a protein concentration of 0.2 mg/mL is added to 380 μL of a substrate solution having the following composition. After carrying out reaction at 30° C. for 1 hour therein, 20 μL of 3N hydrochloric acid is added therein to stop the reaction. Then, into 20 μL of the resultant reaction mixture, a 0.2M sodium carbonate aqueous solution of 80 μL and an acetone solution of 200 μL containing dabsyl chloride by 3.3 mg/mL are added. Then, the resultant mixture is reacted at 70° C. for 10 min. After 20 μL of acetic acid is added therein with stirring. The reaction mixture thus obtained is analyzed by high-performance liquid chromatography thereby to quantitatively analyze dabsylated alanine.

[Substrate Solution Composition]

| | |
|---|---|
| Amino Compound | 14 mM |
| Pyruvic acid | 14 mM |
| Pyridoxal phosphate | 0.02 mM |
| Potassium Phosphate Buffer (pH 7.5) | 0.1M |

[High-Performance Liquid Chromatography Analysis Conditions]

Column: Deverosil ODS-HG-3 (Nomura Chemical Co. Ltd.)
Carrier: Acetonitrile/0.045M acetate buffer (pH 4.1)=35/65 (by volume)
Flow Rate: 0.9 mL/min
Detection: 254 nm Moreover, the enzyme of the present invention is active in case where the amino acceptor is glyoxylic acid instead of 1-benzyl-3-pyrrolidinone or pyruvic acid.

A molecular weight of the enzyme can be determined from a relative elution time to standard protein, which is measured by gel filtration analysis using HiLoad 16/60 Superdex 200 prep grade column (Amersham Biosciences K.K.). As a carrier, the gel filtration analysis uses a 0.01M potassium phosphate buffer (pH 8) containing 0.15M NaCl, 0.01% (v/v) 2-mercaptoethanol, 20 mM pyridoxal phosphate, and 0.1 mM PMSF. Moreover, a molecular weight of a subunit can be determined from a relative mobility to the standard protein, which is measured by 10% SDS-polyacrylamide gel electrophoresis.

Moreover, the enzyme of the present invention may have the following physical and chemical properties.

(4) Optimum pH: 7 to 9
(5) Optimum Temperature for activity: 30° C. to 50° C.
(6) Thermal Stability: after being treated with pH 7.0 and a temperature of 30° C. to 40° C. for 30 min, the enzyme maintains 90% or more of its activity that the enzyme has before the treatment.

The optimum pH for the enzymic reaction can be determined by measuring, in a range of pH 4.0 to pH 11.0, the amino group transfer activity in amino group transfer using (S)-α-phenethylamine and 1-benzyl-3-pyrrolidinone. The measurement of the optimum pH uses the following buffers for the substrate solution depending on pH at which the measurement is carried out.

pH 4.0 to pH 6.0: 0.1M sodium acetate buffer
pH 6.0 to pH 8.5: 0.1M potassium phosphate buffer
pH 8.0 to pH 9.0: 0.1M tris hydrochloride buffer
pH 9.0 to pH 11.0: 0.1M sodium carbonate buffer The optimum temperature for the enzymic reaction can be determined by measuring, at a reaction temperature in a range of 20° C. to 60° C., the amino group transfer activity in amino group transfer using (S)-α-phenethylamine and 1-benzyl-3-pyrrolidinone.

The thermal stability of the enzyme can be determined by measuring the amino group transfer activity with the purified enzyme adjusted to a protein concentration of 2 mg/mL with 0.1M potassium phosphate buffer (pH 7.5) containing 0.02 mM pyridoxal phosphate and then treated with a temperature in a range of 20° C. to 70° C. for 30 min.

In general, a higher concentration of pyridoxal phosphate in the reaction solution would improve the optimum temperature and thermal stability of the aminotransferase.

Further, the enzyme of the present invention can catalyze an amino group transfer reaction in which a ketone compound other than 1-benzyl-3-pyrrolidinone is reacted with (S)-α-phenethylamine as the amino donor, so as to produce acetophenone and an amino compound corresponding to the ketone compound.

The enzyme of the present invention may be any enzyme, provided that it has the properties described above. For example, the enzyme of the present invention can be obtained from microorganisms belonging to *Pseudomonas* sp. One preferable example of the microorganisms which can be the origin of the enzyme of the present invention is *Pseudomonas*

*fluorescens*. More preferably, the enzyme of the present invention may be obtained from *Pseudomonas fluorescens* KNK08-18.

*Pseudomonas fluorescens* KNK08-18 is deposited with Accession No. FERM BP-10599 at International Patent Organism Depository (IPOD) of the National Institute of Advanced Industrial Science and Technology, whose address is Chuodairoku 1-1-1, Higashi, Tsukuba-shi, Ibaragi Prefecture, Japan (Post Code 305-8566) (the strain was originally deposited domestically on Oct. 5, 2004, and then transferred to international depository under the Budapest Treaty on Apr. 27, 2006).

As to medium for the microorganism having the enzyme of the present invention, a liquid nutrition medium containing generally-used carbon source, nitrogen source, an inorganic salt, organic nutrition, and/or the other, provided that the microorganism can grow therein.

The culturing of the microorganism may be preceded by culturing the microorganism in a medium in which an inducing material for the enzyme of the present invention is added therein. Examples of the inducing material encompass propylamine, 1-butylamine, 2-butylamine, 2-pentylamine, isopropylamine, isobutylamine, 7-methoxy-2-aminotetralin, and the like. The inducing materials may be used solely or in combination. There is no particular limitation as to how much the inducing material is added. Considering inhibition of growth of the microorganism or the other factors, it is preferable that the inducing material be added by 1% by weight or less in the normal medium composition. Moreover, there is no particular limitation as to timing of the addition of the inducing material, and the inducing material may be added when the culturing is started, or during the culturing.

Purification of the enzyme of the present invention from the microorganism having the enzyme can be done by a well-known protein purification technique. In the following, a technique for obtaining a polypeptide of the present invention is exemplified. This technique uses *Pseudomonas fluorescens* KNK08-18. It should be noted that the present invention is not limited to this technique.

Firstly, *Pseudomonas fluorescens* KNK08-18 was inoculated in a 50 mL medium in 500 mL Sakaguchi flask (composition: 5 g/L $KH_2PO_4$, 5 g/L $K_2HPO_4$, 0.16 g/L $MgSO_4 \cdot 7H_2O$, 0.018 g/L $FeSO_4 \cdot 7H_2O$, 0.012 g/L $ZnSO_4 \cdot H_2O$, 0.002 g/L $MnSO_4 \cdot 7H_2O$, 0.001 g/L $CuSO_4 \cdot 7H_2O$, 0.02 g/L NaCl, 20 g/L glycerin, 10 g/L yeast extract (Nihon Pharmaceutical Co. Ltd.), 500 mg/L (S)-7-methoxy-2-aminotetralin (pH 7.2)). Then, it is incubated at 30° C. for 1 day thereby to obtain the culture broth. Next, the culture broth is inoculated in a 3.0 L medium (having the same composition) in 5 L mini jar and incubated at 30° C. under air ventilation of 0.6 vvm and stirring of 400 rpm for 28 hours.

Then, the cells are collected from the culture broth centrifugally and suspended in a 0.01M potassium phosphate buffer (pH 8.0) containing 0.01% 2-mercaptoethanol and 0.02 mM pyridoxal phosphate. The dispersion solution thus obtained is subjected to ultrasonic disintegration. Then, solid materials in the liquid subjected to the ultrasonic disintegration are removed centrifugally, thereby obtaining a cell-free extract solution. Then, protamine sulfate is added in the cell-free extract solution thereby to remove nucleic acid therefrom.

The enzyme of the present invention can be purified by subjecting the resultant protamine sulfate-treated liquid to a column chromatography, whose typical examples are ion-exchange chromatography, adsorption chromatography, hydrophobic chromatography, and the like.

One example of the enzyme obtained in this way is an enzyme formed from the amino acid sequence listed as SEQ ID NO: 1 in the sequence list. However, the enzyme of the present invention is not limited to this and encompass enzymes formed from amino acid sequences in which one or some amino acids are deleted, replaced, inserted, or added in the amino acid sequence of SEQ ID NO: 1, provided that the enzyme has amino group transfer reaction activity for producing acetophenone and 1-benzyl-3-aminopyrrolidine from 1-benzyl-3-pyrrolidinone and optically active (S)-α-phenethylamine.

Polypeptides formed from the amino acid sequences in which one or some amino acids are deleted, replaced, inserted, or added in the amino acid sequence of SEQ ID NO: 1 can be prepared from the amino acid sequence of SEQ ID NO: 1 according to well-known methods described in literatures on experiments such as Current Protocols in Molecular Biology (John Wiley and Sons, Inc., 1989).

There is no particular limitation as to site(s) at which the one or some amino acids are deleted, replaced, inserted, or added. However, it is preferable that the site(s) be out of high-preservation region. The "high-preservation region" is location in which amino acids in an amino acid sequence of one aminotransferase derived from one origin are identical with amino acids in an amino acid sequence of another aminotransferase derived from another origin when the amino acid sequences are compared in optimum alignment.

The number of the amino acids deleted, replaced, inserted, or added is preferably 10 or less, more preferably 5 or less, and further preferably 3 or less. The modified amino acid sequence may have one modification (e.g., replacement) or two more modifications (e.g., replacement and insertion). Moreover, it is preferable in the replacement that the replacing amino acid(s) and the replaced amino acid(s) be homogeneous with each other.

A DNA of the present invention is a DNA for encoding the polypeptide, and may be any DNA, provided that it can express the polypeptide in a host cell in which it is introduced by a method described later. The DNA of the present invention may include any non-translation region. If the polypeptide can be obtained via purification, a person skilled in the art can adopt a well known method to obtain such a DNA from a microorganism from which the polypeptide is derived.

It should be noted that the present invention is not limited to the later-described example using *Pseudomonas fluorescens* KNK08-18 (FERM BP-10599).

Firstly, the polypeptide (enzyme) purified from the cell-free extract prepared from the microorganism is digested with an appropriate endopeptidase, thereby cleaving the polypeptide into fragments, which are then purified via reverse-phase HPLC. Then, part of the amino acid sequence thereof is determined by, for example, protein sequencer ABI492 (Applied Biosystems). From the amino acid sequence information thus obtained, PCR (Polymerase Chain Reaction) primers for amplifying part of DNA that encodes the polypeptide is synthesized. Next, using a general DNA isolation method, for example, a method introduced by Murray et al. (Nucl., Acids Res., 8, 4321-4325, 1980), a genomic DNA of the microorganism is prepared. Using this genomic DNA as a template, PCR is carried out with the PCR primers, thereby to amplify the part of the DNA that encodes the polypeptide. In this ways, a base sequence of the part of the DNA is determined. The base sequence can be determined by using the DNA Sequencer ABI373A (Applied Biosystems) or the like.

Once the base sequence of part of the DNA that encodes the polypeptide, it is possible to determine a whole sequence thereof by, for example, Inverse-PCR (Nucl. Acids Res. 16,8186 (1988)).

One example of DNA obtainable in this way is the DNA having the base sequence of SEQ ID NO: 2 in the sequence list. The DNA of the present invention is not limited to this example and encompasses any DNA that encodes the polypeptide of the present invention. For example, the present invention encompasses DNA that is hybridizable with the DNA having a base sequence complementary with the base sequence of SEQ ID NO: 2 in the sequence list under stringent conditions and that encodes a polypeptide having an activity to produce acetophenone and 1-benzyl-3-aminopyrrolidine from 1-benzyl-3-pyrrolidinone and optically active (S)-α-phenethylamine.

Here, the "DNA that is hybridizable with the DNA having a base sequence complementary with the base sequence of SEQ ID NO: 2 in the sequence list under stringent conditions" is a DNA that contains the base sequence complementary with the base sequence of SEQ ID NO: 2 in the sequence list and forms a hybrid when treated with a colony hybridization method, plaque hybridization method, or southern hybridization method, or the like.

An example of the "stringent conditions" is such conditions that hybridization is carried out at 65° C. in the presence of NaCl of 0.7M to 1.0M with a filter on which a polynucleotide derived from a colony or plaque is immobilized, and then the filter is washed at 65° C. with a 2×SSC solution (a 1×SSC solution contains 150 mM sodium chloride and 15 mM sodium citrate). A preferable example thereof is such conditions that the post-hybridization washing is carried out at 65° C. with a 0.5×SSC solution. A more preferable example thereof is such conditions that the post-hybridization washing is carried out at 65° C. with a 0.2×SSC solution. A furthermore preferable example thereof is such conditions that the post-hybridization washing is carried out at 65° C. with a 0.1×SSC solution.

A vector of the present invention may be any vector that can introduce the DNA into a host cell so as to express a polypeptide encoded the DNA in the host cell. Examples of such a vector DNA encompass a plasmid vector, phage vector, cosmid vector, and the like. Moreover, a shuttle vector, which can exchange a gene with another host strain, can be used as the vector of the present invention.

Preferably the vector may contain a workably-bonded control factor such as a promoter (e.g. lacUV5 promoter, trp promoter, trc promoter, tac promoter, 1 pp promoter, tufB promoter, recA promoter, pL promoter), so that the vector contains an expression unit bonded workably with the DNA of the present invention. For example, pUCNT (WO94/03613) and the like can be used preferably.

The term "control factor" used herein is a base sequence having a functional promoter and a given relating transcription element (e.g., enhancer, CCAAT box, TATA box, SPI site, etc.).

The term "workably bonded" used herein means that the gene and an adjusting element of various type such as the promoter, enhancer, or the like, which adjusts the expression of the gene, are bonded with each other in such a manner that they can work in the host cell. A person skilled in the art can understand that the type and kind of the control factor is variable depending on the host.

Examples of the host cell applicable in the present invention encompass microorganism cells such as bacteria, yeasts, filamentous bacteria, and the like, plant cells, animal cells, and the like. The microorganism cells are preferable and *Escherichia coli* is especially preferable. The vector containing the DNA of the present invention can be introduced into the host cells by a well-known method. In the case where the host cell is *Escherichia coli*, the vector can be introduced by, for example, calcium chloride method. Examples of a transformant in which the vector containing the DNA of the present invention encompass *E. coli* HB101 (pNTMTA) (FERM P-20238), and the like.

Next, described is a method for producing an optically active amino compound by using the aminotransferase of the present invention or a microorganism capable of producing the aminotransferase. Examples of the microorganism capable of producing the aminotransferase of the present invention encompass *Pseudomonas fluorescens* KNK08-18 (FERM BP-10599), and the transformant in which the vector containing the DNA of the present invention is introduced.

Examples of the method of the present invention for producing the optically active amino compound encompass a producing method I and a producing method II. The producing method I includes stereo-selectively transferring an amino group from an amino donor to a ketone compound having a main structure identical with that of the targeted amino compound, and then collecting the optically active amino compound thus obtained. The producing method II includes transferring amino group from one of enantiomers in an enantiomer mixture of an amino compound to an amino acceptor selectively, and then collecting the remaining enantiomer (optically active amino compound).

Firstly, the producing method I is described.

According to the producing method, a carbonyl compound is reacted in the presence of the amino donor with the enzyme or a culture product of the microorganism capable of producing the enzyme, the carbonyl compound being represented by General Formula (1):

(1)

where P and Q are an substituted or unsubstituted alkyl group, branched alkyl group, aryl group, heteroaryl group, aryloxy group, heteroaryloxy group, alkoxy group, alkoxycarbonyl group, alkenyl group, alkynyl group, cycloalkyl group, aralkyl group, or heteroaralkyl group, and may form a ring by bonding with each other, but are different from each other in chirality.

This produces an optically active amino compound represented by General Formula (2):

(2)

where P and Q are the same as in General Formula (1).

For example, a carbonyl compound is reacted in the presence of the amino donor with the enzyme or a culture product of the microorganism capable of producing the enzyme, the carbonyl compound being represented by General Formula (3):

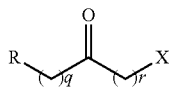

(3)

where q is an integer of 0 to 7, r is an integer of 0 to 2, R is a substituted or unsubstituted aryl group of carbon number of 6 to 14, heteroaryl group of carbon number of 4 to 14, aryloxy group of carbon number of 6 to 14, heteroaryloxy group of carbon number of 4 to 14, alkoxy group of carbon number of 1 to 5, alkoxycarbonyl group of carbon number of 2 to 5, branched alkyl group of carbon number of 3 to 5, alkenyl group of carbon number of 2 to 5, alkynyl group of carbon number of 2 to 5, cycloalkyl group of carbon number of 5 to 7, methyl group, or carboxyl group, X is a hydrogen atom or a substituted or unsubstituted methyl group, and q≧r if R is the methyl group.

This produces an optically active amino compound represented by General Formula (4):

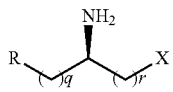

(4)

where q, r, R and X are the same as in General Formula (3).

In General Formulae (3) and (4), q is an integer of 0 to 7, r is an integer of 0 to 2, R is a substituted or unsubstituted aryl group of carbon number of 6 to 14, heteroaryl group of carbon number of 4 to 14, aryloxy group of carbon number of 6 to 14, heteroaryloxy group of carbon number of 4 to 14, alkoxy group of carbon number of 1 to 5, alkoxycarbonyl group of carbon number of 2 to 5, branched alkyl group of carbon number of 3 to 5, alkenyl group of carbon number of 2 to 5, alkynyl group of carbon number of 2 to 5, cycloalkyl group of carbon number of 5 to 7, methyl group, or carboxyl group, X is a hydrogen atom or a substituted or unsubstituted methyl group, and q≧r if R is the methyl group.

The aryl group of carbon number of 6 to 14 may be a phenyl group, naphthyl group, or the like. The heteroaryl group of carbon number of 4 to 14 may be a pyridyl group, thienyl group, oxadiazolyl group, imidazolyl group, thiazolyl group, furyl group, pyroly group, or the like. The aryloxy group of carbon number of 6 to 14 may be a phenoxy group, naphtoxy group or the like. The heteroaryloxy group of carbon number of 1 to 4 may be a pyrridyloxy group, thienyloxy group, oxadiazolyloxy group, imidazolyloxy group, thiazolyloxy group, furyloxy group, pyrrolyloxy group, or the like. The alkoxy group of carbon number of 1 to 5 may be a methoxy group, ethoxy, group, tert-butoxy group, or the like. The alkoxycarbonyl group of carbon number of 2 to 5 may be a methoxycarbonyl group, ethoxycarbonyl group, tert-butoxy- carbonyl group, or the like. The branched alkyl group of carbon number of to 5 may be an isopropyl group, sec-butyl group, tert-butyl group, or the like. The alkenyl group of carbon number of 2 to 5 may be a vinyl group, allyl group, or the like. The alkynyl group of carbon number of 2 to 5 may be acethylene group or the like. The cycloalkyl group of carbon number of 5 to 7 may be cyclopentyl group, cyclohexyl group, cycloheptyl group, or the like. Note that the carbon number of the alkoxycarbonyl group includes the carbonyl carbon.

These groups may be a substituted group with a substituent. Examples of the substituent encompass a halogen atom, a hydroxyl group, an alkoxy group of carbon number of 1 to 4 (such as methoxy group, ethoxy group, methylenedioxy group, or the like), and the other.

Among the ketone compounds represented by General Formula (3), compounds wherein X is a hydrogen atom and r is 1 or 2 are preferable. Specific thereof examples encompass 2-butanone, 2-pentanone, 2-hexanone, 2-heptanone, 2-octanone, 3-hexanone, 3-heptanone, 3-octanone, methoxypropanone, 1-methoxy-2-butanone, 1-methoxy-3-butanone, acetophenone, 2-chloroacetophenone, 3-chloroacetophenone, 4-chloroacetophenone, 2-hydroxyacetophenone, 3-hydroxyacetophenone, 4-hydroxyacetophenone, 2-methoxyacetophenone, 3-methoxyacetophenone, 4-methoxyacetophenone, 2,4-dimethoxyacetophoe, 3,4-di methoxyacetophenone, 2-trifluoro methylacetophenone, 3-trifluoromethylacetophenone, 4- trifluoromethylacetophenone, phenylacetone, 2- chlorophenylacetone, 3-chlorophenylacetone, 4-chlorophenylacetone, 2-hydroxyphenylacetone, 3-hydroxyphenylacetone, 4-hydroxyphenylacetone, 2-methoxyphenylacetone, 3-methoxyphenylacetone, 4-methoxyphenylacetone, 2,4-dimethoxyphenylacetone, 3,4-dimethoxyphenylacetone, 2-trifluoromethylphenylacetone, 3-trifluoromethylphenylacetone, 4-trifluoromethylphenylacetone, benzylacetone, 2-chlorobenzylacetone, 3-chlorobenzylacetone, 4-chlorobenzylacetone, 2-hydroxybenzylacetone, 3-hydroxybenzylacetone, 4- hydroxybenzylacetone, 2-methoxybenzylacetone, 3- methoxybenzylacetone, 4-methoxybenzylacetone, 2,4-dimethoxybenzylacetone, 3,4- dimethoxybenzylacetone, 2-trifluoromethylbenzylacetone, 3-trifluoromethylbenzylacetone, 4-trifluoromethylbenzylacetone, 1-naphthylacetone, 2-naphthylacetone, 2-acetylpyridine, 3-acetylpyridine, 4-acetylpyridine, acetylpyrazine, 2-acetylfuran, 3-acethylfuran, 2-acethylthiophene, 3-acethylthiophene, 2-acethylthiazole, benzoyl ethyl acetate, and the like.

Moreover, the producing method I may be arranged such that a carbonyl compound is reacted in the presence of the amino donor with the enzyme or a culture product of the microorganism capable of producing the enzyme, the carbonyl compound being represented by General Formula (7):

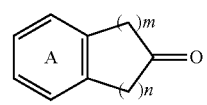

(7)

This produces an optically active amino compound represented by General Formula (8):

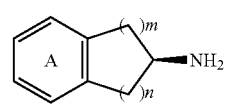

(8)

In General Formulae (7) and (8), m is an integer of 0 to 3, n is an integer of 2 to 4 (where n>m), and the ring A is a benzene ring unsubstituted or substituted with a halogen atom, a hydroxyl group, an alkoxy group of carbon number of 1 to 4 (methoxy group, ethoxy group, methylenedioxy group, or the like), or the like.

Among the ketone compounds represented by General Formula (7), compounds wherein m is 1 and n is 2 is preferable. Specific examples of the compounds encompass: 1-indanone, 4-methoxy-1-indanone, 5-methoxy-1-indanone, 6-methoxy-1-indanone, 7-methoxy-1-indanone, 2-tetralone, 5-methoxy-2-tetralone, 6-methoxy-2-tetralone, 7-methoxy-2-tetralone, 8-methoxy-2-tetralone, 5-hydroxy-2-tetralone, 6-hydroxy-2-tetralone, 7-hydroxy-2-tetralone, 8-hydroxy-2-tetralone, 1-tetralone, 5-methoxy-1-tetralone, 6-methoxy-1-tetralone, 7-methoxy-1-tetralone, 8-methoxy-1-tetralone, and the like. More preferable are 1-tetralone, 2-tetralone, 5-methoxy-2-tetralone, 6-methoxy-2-tetralone, 7-methoxy-2-tetralone, and 8-methoxy-2-tetralone. 7-methoxy-2-aminotetralin is most preferable.

Furthermore, the producing method I may be arranged such that a carbonyl compound is reacted in the presence of the amino donor with the enzyme or a culture product of the microorganism capable of producing the enzyme, the carbonyl compound being represented by General Formula (11):

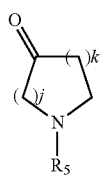
(11)

This produces an optically active amino compound represented by General Formula (12):

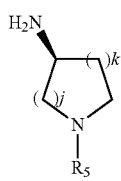
(12)

In General Formulae (11) and (12), j and k are independently an integer of 1 to 3 (where k≧j), $R_5$ is a hydrogen atom, aryl group of carbon number of 6 to 14, heteroaryl group of carbon number of 4 to 14, alkyl group of carbon number of 1 to 6, alkoxy group of carbon number of 1 to 6, acyl group of carbon number of 2 to 15, alkoxycarbonyl group of carbon number of 1 to 6, aralkyl group of carbon number of 7 to 15, aralkyloxycarbonyl group of carbon number of 8 to 16, or a sulfonyl group substituted with an alkyl group of carbon number of 1 to 6 or aryl group of carbon number of 6 to 14.

The aryl group of carbon number of 6 to 14 may be a phenyl group, naphthyl group, or the like. The heteroaryl group of carbon number of 4 to 14 may be a pyridyl group, thienyl group, oxadiazolyl group, imidazolyl group, thiazolyl group, furyl group, pyrrolyl group, or the like. The alkyl group of carbon number of 1 to 6 may be a methyl group, ethyl group, n-propyl group, isopropyl group, n-butyl group, sec-buthyl group, tert-butyl group, or the like. The alkoxy group of carbon number of 1 to 6 may be a methoxy group, ethoxy group, tert-butoxy group, or the like. The acyl group of carbon number of 2 to 15 may be acetyl group, pivaloyl group, benzoyl group, or the like. The alkoxycarbonyl group of carbon number of 1 to 6 may be a methoxycarbonyl group, ethoxycarbonyl group, tert-butoxycarbonyl group, or the like. The aralkyl group of carbon number of 7 to 15 may be benzyl group or the like. The aralkyloxy group of carbon number of 8 to 16 may be benzyloxycarbonyl group or the like. The sulfonyl group substituted with an alkyl group of carbon number of 1 to 6 or aryl group of carbon number of 6 to 14 may be a mesyl group, tosyl group, or the like. Note that the carbon numbers of the acyl group, alkyloxy group, and aralkyloxy group include the carbonyl carbon.

Among the ketone compound represented by General Formula (11), compounds wherein j is 1 and k is 2 is preferable. Moreover, compounds wherein $R_5$ is a hydrogen atom, phenyl group, benzyl group, benzoyl group, benzyloxycarbonyl group, tert-butoxycarbonyl group, mesyl group, or tosyl group are preferable. Specific examples thereof encompass: 1-benzyl-3-pyrrolidinone, 1-tert-butoxycarbonyl-3-pyrrolidinone, 1-tosyl-3-pyrrolidinone, 1-mesyl-3-pyrrolidinone, 1-benzyloxycarbonyl-3-pyrrolidinone, 3-pyrrolidinone, and the like. 1-benzyl-3-pyrrolidinone is more preferable.

The amino donor may be an amine group represented by General Formula (15):

(15)

where $R_6$ and $R_7$ are independently a hydrogen atom or a substituted or unsubstituted carboxyl group, alkyl group of carbon number of 1 to 10, cycloalkyl group of carbon number of 5 to 7, aralkyl group of carbon number of 7 to 15, or aryl group of carbon number of 6 to 14.

The alkyl group of carbon number of 1 to 10 may be a methyl group, ethyl group, n-propyl group, isopropyl group, n-butyl group, sec-butyl group, tert-butyl group, or the like. The cycloalkyl group of carbon number of 5 to 7 may be cyclopentyl group, cyclohexyl group, cycloheptyl group, or the like. The aralkyl group of carbon number of 7 to 15 may be benzyl group or the like. The aryl group of carbon number of 6 to 14 may be phenyl group, naphthyl group or the like.

In the amine compounds represented by General Formula (15), it is preferable that $R_6$ be a substituted or unsubstituted, straight or branched alkyl group of carbon number of 1 to 10, or a substituted or unsubstituted aryl group of carbon number of 6 to 10, and it is more preferable that $R_6$ be a substituted or unsubstituted alkyl group of carbon number of 1 to 5, or phenyl group. It is preferable that $R_7$ be a hydrogen atom, a carboxyl group, or a substituted or unsubstituted alkyl group of carbon number of 1 or 2. It is more preferable that $R_7$ be a hydrogen atom or a methyl group.

Specific examples of the compound represented by General Formula (15) encompass α-phenethylamine, 2-butylamine, 2-pentylamine, 2-heptylamine, 2-octylamine, alanine, glycin, n-propylamine, n-butylamine, n-amylamine, isopropylamine, benzylamine, β-phenethylamine, and optically active isomers thereof. Among them, α-phenethylamine is preferable, and (S)-α-phenethylamine is more preferable.

In the producing method I, in the presence of the amino donor represented by General Formula (15), the ketone compound represented by General Formula (1), (3), (7), or (11) is reacted with the enzyme of the present invention or the culture product of the microorganism capable of producing the enzyme. Here, the "culture product" means (i) a culture broth containing the cells, (ii) incubated cells, or (iii) a material prepared therefrom. The "material prepared therefrom" means, for example, a cell-free extract solution, freeze-dried cells, acetone-dried cells, or a ground product of such dried cells, and the like. Moreover, the enzyme and culture product may be immobilized by a well-known method so as to be used immobilized enzyme or immobilized microorganism. The immobilization may be carried out by a method well known among persons skilled in the art (e.g., cross-linking method, physical adsorption method, entrapment method, or the like).

As to concentration of the substrate used in the reaction mixture, the ketone compound is in a range of 0.1 to 20% by weight or preferably in a range of 1 to 10% by weight in the reaction solution. If the amino donor is a chiral amine, concentration of the amino donors is in a range of 80 to 1200 mol %, or preferably in a range of 100 to 600 mol % in relation to the ketone compound. Moreover, if the amino donor is a racemic amine compound, one of enantiomers may have the concentration as specified above.

Considering optimum pH of the enzyme, pH at which the enzyme of the present invention works is preferably 5.0 or more and more preferable 6.0 or more at lowest, and is preferably 10.0 or less and more preferably 9.0 or less at highest.

Considering the optimum temperature and thermal stability of the enzyme, a temperature at which the enzyme of the present invention works is preferably 25° C. or higher and more preferably 30° C. or higher, and is preferably 60° C. or lower and more preferably 50° C. or lower.

A reaction solvent is generally an aqueous solvent such as ion-exchanged water, a buffer solution, or the like. However, the reaction may be carried out in a system containing an organic solvent. The organic solvent may be, for example, an alcohol solvent such as methanol, ethanol, propanol, isopropanol, butanol, or the like, an aliphatic hydrocarbon solvent such as pentane, hexane, or the like, an aromatic hydrocarbon solvent such as benzene, toluene, or the like, a halogenated hydrocarbon such as methylene chloride, chloroform, or the like, an ether solvent such as diethylether, diisopropylether, or the like, an ester solvent such as ethyl acetate, butyl acetate, or the like, a ketone solvent such as acetone, methylethylketone, or the like, acetonitrile, or the other organic solvent.

The reaction may be carried out in a two-phase system by adding such an organic solvent in an amount equal to or greater than its solubility to water. In a reaction system in which such an organic solvent is coexisted, there are many cases that selective rates, transfer rates, yields or the other factors are improved.

The reaction provides the optically active amino compound represented by General Formula (2), (4), (8), or (12). The optically active amino compound thus obtained can be isolated from the reaction mixture via a well-known method such as extraction, distillation, recrystallization, column separation, or the like.

For example, after pH acidification, unreacted substrate and the ketone compound obtained via the amino group transfer reaction from the amino donor can be removed into a general solvent while the obtained optically active amino compound in the water phase, the general solvent being an ether such as diethyl ether, diisopropylether, or the like, an ester such as ethyl acetate, butyl acetate, or the like, a hydrocarbon such as hexane, octane, benzene, or the like, a halogenated hydrocarbon such as methylene chloride or the like, or the other solvent. The resultant optically active amino compound and the unreacted amino donor can be separated by, for example, distillation.

Next, the producing method II of the present invention is described.

In the producing method II, an enantiomer mixture of an amino compound is reacted in the presence of the amino acceptor with the enzyme or a culture product of the microorganism capable of producing the enzyme, the amino compound being represented by General Formula (5):

(5)

This produces an optically active amino compound represented by General Formula (6):

(6)

In General Formulae (5) and (6), q, r, R, and X are identical with q, r, R, and X in General Formulae (3) and (4).

Among the amino compounds represented by General Formula (5), compounds wherein X is a hydrogen atom and r is 1 or 2 are preferable. Specific examples thereof encompass 2-butylamine, 2-pentylamine, 2-hexylamine, 2-heptylamine, 2-octylamine, 3-hexylamine, 3-heptylamine, 3-octylamine, methoxypropylamine, 1-methoxy-2-butylamine, 1-methoxy-3-butylamine, α-phenethylamine, 2-chloro-α-phenethylamine, 3-chloro-α-phenethylamine, 4-chloro-α-phenethylamine, 2-hydroxy-α-phenethylamine, 3-hydroxy-α-phenethylamine, 4-hydroxy-α-phenethylamine, 2-methoxy-α-phenethylamine, 3-methoxy-α-phenethylamine, 4-methoxy-α-phenethylamine, 2,4-dimethoxy-α-phenethylamine, 3,4-dimethoxy-α-phenethylamine, 2-trifluoromethyl-α-phenethylamine, 3-trifluoromethyl-α-phenethylamine, 4-trifluoromethyl-α-phenethylamine, 1-phenyl-2-aminopropane, 1-(2-chlorophenyl)-2-aminopropane, 1-(3-chlorophenyl)-2-aminopropane, 1-(4-chlorophenyl)-2-aminopropane, 1-(2-hydroxyphenyl)-2-aminopropane, 1-(3-hydroxyphenyl)-2-aminopropane, 1-(4-hydroxyphenyl)-2-aminopropane, 1-(2-methoxyphenyl)-2-aminopropane, 1-(3-methoxyphenyl)-2-aminopropane, 1-(4-methoxyphenyl)-2-aminopropane, 1-(2,4-dimethoxyphenyl)-2-aminopropane, 1-(3,4-dimethoxyphenyl)-2-aminopropane, 1-(2-trifluoromethylphenyl)-2-aminopropane, 1-(3-trifluoromethylphenyl)-2-aminopropane, 1-(4-trifluoromethylphenyl)-2-aminopropane, 1-phenyl-3-butylamine, 1-(2-chlorophenyl)-3-butylamine, 1-(3-chlorophenyl)-3-butylamine, 1-(4-chlorophenyl)-3-butylamine, 1-(2-hydroxyphenyl)-3-butylamine, 1-(3-hydroxyphenyl)-3-butylamine, 1-(4-hydroxyphenyl)-3-butylamine, 1-(2-methoxyphenyl)-3-butylamine, 1-(3-methoxyphenyl)-3-butylamine, 1-(4-methoxyphenyl)-3-butylamine, 1-(2,3-dimethoxyphenyl)-3-butylamine, 1-(2,4-dimethoxyphenyl)-3-butylamine, 1-(3,4-dimethoxyphenyl)-3-butylamine, 1-(2-trifluoromethylphenyl)-3-butylamine, 1-(3-trifluoromethylphenyl)-3-butylamine, 1-(4-trifluoromethylphenyl)-3-butylamine, 1-(1-naphtyl)-2-aminopropane, 1-(2-naphtyl)-2-aminopropane, 1-(2-pyridyl)ethylamine, 1-(3-pyridyl)ethylamine, 1-(4-pyridyl)ethylamine, 1-pyrazylethylamine, 1-(2-furyl)ethylamine, 1-(3-furyl)ethylamine, 1-(2-thienyl)ethylamine, 1-(3-thienyl)ethylamine, 1-(2-thiazolyl)ethylamine, β-phenylalanine, and the like.

Moreover, the producing method II may be arranged such that an enantiomer mixture of an amino compound is reacted in the presence of the amino acceptor with the enzyme or a culture product of the microorganism capable of producing the enzyme, the amino compound being represented by General Formula (9):

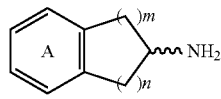

(9)

This produces an optically active amino compound represented by General Formula (10):

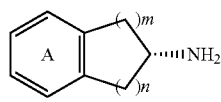

(10)

In General Formulae (9) and (10), m, n, and the ring A are identical with m, n, and the ring A in General Formulae (7) and (8).

Among the amino compound represented by General Formula (9), compounds wherein m is 1 and n is 2 are preferable. Specific examples thereof encompass 1-aminoindan, 4-methoxy-1-aminoindan, 5-methoxy-1-aminoindan, 6-methoxy-1-aminoindan, 7-methoxy-1-aminoindan, 2-aminotetralin, 5-methoxy-2-aminotetralin, 6-methoxy-2-aminotetralin, 7-methoxy-2-aminotetralin, 8-methoxy-2-aminotetralin, 5-hydroxy-2-aminotetralin, 6-hydroxy-2-aminotetralin, 7-hydroxy-2-aminotetralin, 8-hydroxy-2-aminotetralin, 1-aminotetralin, 5-methoxy-1-aminotetralin, 6-methoxy-1-aminotetralin, 7-methoxy-1-aminotetralin, 8-methoxy-1-aminotetralin, and the like. More preferable are 1-aminotetralin, 2-aminotetralin, 5-methoxy-2-aminotetralin, 6-methoxy-2-aminotetralin, 7-methoxy-2-aminotetralin, and 8-methoxy-2-aminotetralin. 7-methoxy-2-aminotetralin is most preferable.

Furthermore, the producing method II may be arranged such that an enantiomer mixture of an amino compound is reacted in the presence of the amino acceptor with the enzyme or a culture product of the microorganism capable of producing the enzyme, the amino compound being represented by General Formula (13):

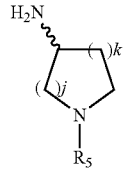

(13)

This produces an optically active amino compound represented by General Formula (14):

(14)

In General Formulae (13) and (14), j, k, and $R_5$ are identical with j, k, and $R_5$ in General Formulae (11) and (12).

Among the amino compounds represented by General Formula (13), compounds wherein j is 1 and k is 2 are preferable. Moreover, compounds are preferable in which $R_5$ is a hydrogen atom, phenyl group, benzyl group, benzoyl group, benzyloxycarbonyl group, tert-butoxycarbonyl group, mesyl group, or tosyl group. Specific examples thereof encompass 1-benzyl-3-aminopyrrolidine, 1-tert-butoxycarbonyl-3-aminopyrrolidine, 1-tosyl-3-aminopyrrolidine, 1-mesyl-3-aminopyrrolidine, 1-benzyloxycarbonyl-3-aminopyrrolidine, and 3-aminopyrrolidine. 1-benzyl-3-aminopyrrolidine is preferable.

In the producing method II, the ketone compound acts as the amino acceptor. Any ketone compound can be adopted therein, provided that it can act as an amino acceptor. The ketone compound is preferably pyruvic acid or glyoxylic acid.

In the producing method II, an enantiomer mixture of the amino compound is reacted in the presence of the amino acceptor with the enzyme or a culture product of the transformant capable of producing the enzyme, the amino compound being represented by General Formula (5), (9), or (13).

Here, the enantiomer mixture of the amino compound represented by General Formula (5), (9), or (13) is a mixture of an enantiomer represented by General Formula (6), (10), or (14) and its enantiomeric isomer. In general, racemates, which are low in cost and easy to obtain, are preferable. However, the present invention is not limited to recemates, and may be arranged such that a mixture containing the enantiomer represented by General Formula (6), (10), or (14) slightly more than its enantiomeric isomer is used. This increase the optical purity by the producing method II.

Moreover, the "culture product" means the same as in the producing method I.

In the reaction, concentration of amino compound (5), (9), or (13) is in a range of 0.1% to 20% by weight, and preferably in a range of 1% to 10% by weight in the reaction solution composition. Moreover, concentration of the amino acceptor is in a range of 30 to 100 mol %, and preferably in a range of 50 to 60 mol % in relation to the amino compound.

The producing method II is identical with the producing method I as to reaction pH, reaction temperature, and reaction solvent.

Via the reaction described above, the optically active amino compound represented by General Formula (6), (10), or (14) is produced. The optically active amino compound thus obtained can be isolated from the reaction mixture in the same manner in the producing method I.

Yield and purity of the optically active amino compounds thus produced via the producing methods I and II can be evaluated, for example, via quantitative analysis carried out by subjecting the reaction solution to separation using a reverse-phase column (Cosmosil 5C18-AR, Nacalai Tesque Inc., or the like) 25% acetonitrile or the like as its mobile phase, and then comparing adsorption thereof at 210 nm with a control. Optical purity can be measured by forming a diastereomer by bonding the obtained amino compound with N-carboxy-L-leucine anhydride or the like, and subjecting the diastereomer to high-performance liquid chromatography using a reverse phase column (Cosmosil 5C18-AR, Nacalai Tesque Inc., or the like).

EXAMPLE

In the following, the present invention is described in more details referring to Examples, which are not to limit the present invention.

Example 1

Preparation of Purified Enzyme

*Pseudomonas fluorescens* KNK08-18 (FERM BP-10599) isolated from soil was inoculated in a 50 mL S17 medium in 500 mL Sakaguchi flask (composition: 5 g/L $KH_2PO_4$, 5 g/L $K_2HPO_4$, 0.16 g/L $MgSO_4.7H_2O$, 0.018 g/L $FeSO_4.7H_2O$, 0.012 g/L $ZnSO_4.H_2O$, 0.002 g/L $MnSO_4.7H_2O$, 0.001 g/L 1 $CuSO_4.7H_2O$, 0.02 g/L NaCl, 20 g/L glycerin, 10 g/L yeast extract (Nihon Pharmaceutical Co. Ltd.), 500 mg/L (S)-7-methoxy-2-aminotetralin (pH 7.2).) Then, it was incubated at 30° C. for 1 day thereby to obtain the culture broth. Next, the culture broth was inoculated in a 3.0 L medium (having the same composition) in 5 L mini jar and incubated at 30° C. under air ventilation of 0.6 vvm and stirring of 400 rpm for 28 hours. Then, the cells were collected from the culture broth centrifugally and suspended in a 0.01M potassium phosphate buffer (pH 8.0) containing 0.01% 2-mercaptoethanol and 0.02 mM pyridoxal phosphate. The dispersion solution thus obtained was subjected to ultrasonic disintegration. Then, solid materials in the solution subjected to the ultrasonic disintegration were removed centrifugally, thereby obtaining a cell-free extract solution.

Then, protamine sulfate was added in the cell-free extract solution thereby to remove nucleic acid therefrom. Into the protamine sulfate-treated solution, ammonium sulfate was added to 30% saturation and dissolved thereby obtaining precipitates, which was then centrifugally removed. Into a supernatant thus obtained, ammonium sulfate was added to 60% saturation and dissolved therein, thereby obtaining precipitates, which was then centrifugally collected.

The precipitates were dissolved in a 10 mM phosphate buffer (pH 8.0) containing 0.01% 2-mercaptoethanol, 20 mM pyridoxal phosphate, and 0.1 mM phenylmethylsulfonylfluoride (PMSF). Then, the buffer was dialyzed. The dialyzed was introduced in a DEAE-TOYOPEARL 650M (Tosoh Corp.) column (300 mL) equilibrated with the same buffer. Thereby, active fractions of the dialyzed were adsorbed therein. After the column was washed with the same buffer, the active fractions were eluted into sodium chloride solutions with a linear gradient (from 0M to 0.3M).

The eluted active fractions were added together and mixed with ammonium sulfate to final concentration of 1.2M. The resultant solution was introduced into Phenyl-TOYOPEARL 650M (Tosoh Corp.) column (120 mL) equilibrated in advance with a 10 mM phosphate buffer (pH 8.0) containing 1.2M ammonium sulfate, 0.01% 2-mercaptoethanol and 20 mM pyridoxal phosphate, and 0.1 mM PMSF. Thereby, the active fractions were adsorbed therein. After the column with the same buffer, the active fractions were eluted into ammonium sulfate solutions with a linear gradient (from 1.2M to 0M). The eluted active fractions were added together and then dialyzed with a 10 mM phosphate buffer (pH 8.0) containing 0.01% 2-mercaptoethanol and 20 mM pyridoxal phosphate, and 0.1 mM PMSF.

A crude enzyme solution thus obtained was introduced into Q-sepharose 16/10HP column (Amersham Biosciences K.K.) equilibrated in advance with a 10 mM phosphate buffer (pH 8.0) containing 0.01% 2-mercaptoethanol and 20 mM pyridoxal phosphate, and 0.1 mM PMSF. Thereby, the active fractions were adsorbed therein. After the column was washed with the same buffer, the active fractions were eluted into sodium chloride solutions with a linear gradient (from 0 M to 0.7M).

The eluted active fractions were added together and mixed with ammonium sulfate to final concentration of 1.0M, and then introduced into Butyl-TOYOPEARL 650S (Tosoh Corp.) column (25 mL) equilibrated in advance with a 10 mM phosphate buffer (pH 8.0) containing 1.0M ammonium sulfate, 0.01% 2-mercaptoethanol and 20 mM pyridoxal phosphate, and 0.1 mM PMSF. Thereby, the active fractions were adhered therein. After the column was washed with the same buffer, the active fractions were eluted into ammonium sulfate solutions with a linear gradient (from 1.0M to 0M). An active crude enzyme solution was thereby obtained and then concentrated via ultrafiltration.

The crude enzyme solution thus concentrated was introduced into Hi LOAD 16/60 Superdex 200 p/g column (Amersham Biosciences K.K.) equilibrated in advance with a 10 mM phosphate buffer (pH 8.0) containing 0.01% 2-mercaptoethanol and 20 mM pyridoxal phosphate, 0.1 mM PMSF, and 0.15M sodium chloride. Thereby, a purified enzyme sample that was uniform electrophoresis-wise. Hereinafter, the enzyme is referred to as MTA.

Example 2

Physical and Chemical Properties 1 of Purified Enzyme

The purified MTA enzyme thus obtained in Example 1 was evaluated in its physical and chemical properties.

(1) Effect:

The purified enzyme solution was adjusted to a protein concentration of 2 mg/mL. Then 0.1 mL of the enzyme solution was added to a substrate solution of 0.9 mL having the following composition and then reacted at 30° C. One hour later, 0.1 mL of 3N hydrochloric acid was added therein thereby to stop the reaction. The reaction solution thus obtained was analyzed via high-performance liquid chromatography. This confirmed that MTA was capable of causing amino group transfer, acting with optically active (S)-α-phenethylamine and 1-benzyl-3-pyrrolidinone thereby to produce acetophenone and 1-benzyl-3-aminopyrrolidine.

[Substrate Solution Composition]

(S)-α-phenethylamine 28.3 mM 1-benzyl-3-pyrrolidinone 28.3 mM

Pyridoxal phosphate 0.02 mM

Potassium phosphate buffer (pH 7.0) 0.1M

[High-Performance Liquid Chromatography Analysis Conditions]

Column: Finepak SIL C18-T (JASCO Corp.)

Carrier: Distilled Water 1260 mL/Acetonitrile 740 mL/$KH_2PO_4$ 10 g/SDS 2.88 g (pH3.6)

Flow Rate: 1 mL/min

Detection: 254 nm

Column Temperature: 40° C.

(2) Optimum pH:

To find optimum pH of the MTA the amino group transfer activity was measured in a range of pH 4 to 11 in the same manner as above (except that the following buffers were used depending on pH to measure). As a result, it was found that the optimum pH was in a range of 7 to 9.

[Buffers]

pH 4.0 to pH 6.0: 0.1M sodium acetate buffer pH 6.0 to pH 8.5: 0.1M potassium phosphate buffer pH 8.0 to pH 9.0: 0.1M tris hydrochloride buffer pH 9.0 to pH 11.0: 0.1M sodium carbonate buffer (3) Optimum Temperature:

The activity was measured in a temperature range of 20° C. to 70° C. under the same conditions as above (pH 7.0). As a result, it was found that the reaction optimum temperature was in a range of 30° C. to 50° C.

(4) Thermal Stability

The MTA was heated at temperatures of 20° C. to 70° C. for 30 min in a 0.1M phosphate buffer (pH 7.5) containing 0.02M pyridoxal phosphate. Then, the activity was measured under the same conditions (temperature 30° C. and pH 7.0). As a result, it was found that 90% or more of the activity was maintained after the heat treatments with the temperatures of 20° C. to 40° C.

(5) Molecular Weight:

The MTA was measured in molecular weight by a gel filtration method using HiLoad 16/60 Superdex 200 prep grade (Amersham Biosciences K.K.). It was found that the MTA had a molecular weight of approximately 120,000. Moreover, a molecular weight of a subunit thereof was measured by SDS-polyacrylamide gel electrophoresis. It was found that the subunit had a molecular weight of approximately 53,000.

Example 3

Physical and Chemical Property of Purified Enzyme Specificity for Amino Donor

In 20 μL of the purified Enzyme, 380 μL of a 0.1M potassium phosphate buffer containing 14 mM of 7-methoxy-2-tetralone and 14 mM (in case of the racemic amine compound, 28 mM)) of an amine compound of various type was added. After the mixture was reacted at 30° C. for 1 hour, 20 μL of 3N hydrochloric acid was added therein to stop the reaction. The reaction solution thus obtained was analyzed via high-performance liquid chromatography so as to quantitatively analyze 7-methoxy-2-aminotetralin thus obtained. Thereby, the amino group transfer activities with the various amino compounds were analyzed. Results of the analysis are shown in Table 1, in which the amino group transfer activities are shown as relative activities where the activity with (S)-α-phenethylamine is 100. As shown in Table 1, this enzyme showed an especially high activity with (S)-α-phenethylamine.

[Analysis Conditions of High-Performance Liquid Chromatography]

Column: Cosmosil 5C8-MS (Nacalai Tesque Inc.)

Carrier: 30 mM potassium phosphate buffer (pH 2.5)/acetonitrile/methanol=4/1/1 (by volume)

Flow Rate: 0.9 mL/min

Detection: 254 nm

TABLE 1

| Amino Group Donor | Relative Activity (%) |
|---|---|
| ±2-butylamine | 48 |
| ±2-pentylamine | 60 |
| ±2-heptylamine | 93 |
| ±3-heptylamine | 19 |
| n-ethylamine | 6 |
| n-propylamine | 6 |
| n-butylamine | 7 |
| n-amylamine | 11 |
| isopropylamine | 10 |
| isobutylamine | 8 |
| L-alanine | 20 |
| ±3-amino-1-phenylbutane | 90 |
| ±3',4'-dimethoxyamphetamine | 88 |
| benzylamine | 35 |
| β-phenethylamine | 22 |
| cyclohexylamine | 22 |
| β-alanine | 0 |
| DL-lysine | 0 |
| (S)-α-phenethylamine | 100 |

Example 4

Physical and Chemical Property of

Purified Enzyme: Specificity for Amino Donor

The purified enzyme obtained in Example 1 was analyzed in terms of its reactivity to typical substrates of ω-amino acid transaminase. Firstly, 20 μL of a purified enzyme solution having a protein concentration of 0.2 mg/mL was added to 3804 of a substrate solution having the following composition. After carrying out reaction at 30° C. for 1 hour therein, 20 μL of 3N hydrochloric acid was added therein to stop the reaction. Then, into 20 μL of the resultant reaction mixture, a 0.2M sodium carbonate aqueous solution of 80 μL and an acetone solution of 200 μL containing dabsyl chloride by 3.3 mg/mL were added. Then, the resultant mixture was reacted at 70° C. for 10 min. After 20 μL of acetic acid was added therein with stirring. The reaction mixture thus obtained was analyzed by high-performance liquid chromatography thereby to quantitatively analyze dabsylated alanine. Results of the analysis are shown in Table 2, which the amino group transfer activities are shown as relative activities where the activity with (S)-α-phenethylamine as the amino donor is 100. As shown in Table 2, this enzyme showed no activity with Valanine, taurine, putrescine, DL-ornithine, and DL-lysine.

[Substrate Solution Composition]

Amino Compound 14 mM

Pyruvic acid 14 mM

Pyridoxal phosphate 0.02 mM

Potassium Phosphate Buffer (pH 7.5) 0.1M

[High-Performance Liquid Chromatography Analysis Conditions]

Column: Deverosil ODS-HG-3 (Nomura Chemical Co., Ltd.)

Carrier: Acetonitrile/0.045M acetate buffer (pH 4.1)=35/65 (by volume)

Flow Rate: 0.9 mL/min

Detection: 254 nm

TABLE 2

| Amino Group Donor | Relative Activity (%) |
|---|---|
| β-Alanine | 0 |
| Taurine | 0 |
| Putrescine | 0 |
| DL-Ornithine | 0 |
| DL-Lysine | 0 |
| (S)-α-Phenethylamine | 100 |

Example 5

Physical and Chemical Property of Purified Enzyme: Specificity for Amino Acceptor The purified enzyme obtained in Example 1 was analyzed in terms of substrate specificity regarding amino acceptors. In 20 μL of the purified Enzyme, 380 μL of a 0.1M potassium phosphate buffer containing 14 mM of (S)-α-phenethylamine and 14 mM of a ketone compound of various type was added. After the mixture was reacted at 30° C. for 1 hour, 20 μL of 3N hydrochloric acid was added therein to stop the reaction. Results of the analysis are shown in Table 3, in which the relative activities are shown where the activity with pyruvic acid as the amino acceptor is 100. As shown in Table 3, this enzyme showed high activity with pyruvic acid and glyoxylic acid, but no activity with 2-ketoglutaric acid.

[Analysis Conditions of High-Performance Liquid Chromatography]
Column: Cosmosil 5C8-MS (Nacalai Tesque Inc.)
Carrier: 30 mM potassium phosphate buffer (pH 2.5)/acetonitrile/methanol=4/1/1 (by volume)
Flow Rate: 0.9 mL/min
Detection: 254 nm

TABLE 3

| Amino Group Receptor | Relative Activity (%) |
|---|---|
| Pyruvic Acid | 100 |
| 2-Ketoglutaric Acid | 0 |
| Glyoxylic Acid | 99 |
| Propionaldehyde | 5 |
| Butylaldehyde | 18 |
| Benzaldehyde | 2 |
| 2-Ketobutyric Acid | 2 |
| 2-Keto-n-Valeric Acid | 0.1 |

Example 6

Physical and Chemical Property of Purified Enzyme Specificity for Amino Acceptor 2

The purified enzyme obtained in Example 1 was analyzed in terms of substrate specificity regarding amino acceptors in the same manner as in Example 5. Results of the analysis are shown in Table 4.

TABLE 4

| Amino Group Receptor | Relative Activity (%) |
|---|---|
| 2-Heptane | 7 |
| 3'-Methoxyacetophenone | 10 |
| Benzylacetone | 33 |
| 3-Acetylpyridine | 10 |
| Acetylpyrazine | 100 |
| Methoxypropanone | 13 |
| 1-Benzyl-3-Pyrrolidinone | 20 |
| Benzoyl Ethylacetate | 13 |
| 3'-Hydroxyacetophenone | 3 |
| 3'-Trifluoromethylacetophenone | 40 |
| 4'-Chloroacetophenone | 30 |
| 2-Tetralone | 17 |
| 7-Methoxy-2-Tetralone | 10 |

Example 7

Substrate Specificity: Comparison with ω-Amino Acid Transaminase

The purified enzyme obtained in Example 1 was analyzed in terms of its reactivity to typical substrates of ω-amino acid transaminase. Firstly, 20 μL of a purified enzyme solution having a protein concentration of 0.2 mg/mL was added to 380 μL of a substrate solution having the following composition. After carrying out reaction at 30° C. for 1 hour therein, 20 μL of 3N hydrochloric acid was added therein to stop the reaction. Then, into 20 μL of the resultant reaction mixture, a 0.2M sodium carbonate aqueous solution of 80 μL and an acetone solution of 200 μL containing dabsyl chloride by 3.3 mg/mL were added. Then, the resultant mixture was reacted at 70° C. for 10 min. After 20 μL of acetic acid was added therein with stirring. The reaction mixture thus obtained was analyzed by high-performance liquid chromatography thereby to quantitatively analyze dabsylated alanine or glutaric acid. Results of the analysis are shown in Table 5, in which the relative activities are shown where the activity with (S)-α-phenethylamine as the amino donor is 100. In Table 5, the values of activities of ω-amino acid:pyruvic acid transaminase and 4-amino butyric acid: 2-ketoglutaric acid transaminase are from the literatures "Agric. Biol. Chem. 41, 1701-1706 (1977), Arch. Biochem. Biophys. 200, 156-164 (1980)". As shown in Table 5, this enzyme was not reactive with β-alanine, taurine, putrescine, and 4-amino butyric acid, which are typical substrates of ω-amino acid transaminase, but was highly active with (S)-α-phenethylamine.

[Substrate Solution Composition]
Amino Compound 14 mM
Pyruvic acid or 2-ketoglutaric acid 14 mM
Pyridoxal phosphate 0.02 mM
Potassium Phosphate Buffer (pH 7.5) 0.1M

[High-Performance Liquid Chromatography Analysis Conditions]
Column: Deverosil ODS-HG-3 (Nomura Chemical Co., Ltd.)
Carrier: Acetonitrile/0.045M acetate buffer (pH 4.1)=35/65 (by volume)
Flow Rate: 0.9 mL/min
Detection: 254 nm

TABLE 5

| Amino Group Donor | Amino Group Receptor | Enzyme A | B | C |
|---|---|---|---|---|
| (S)-α-Phenethylamine | Pyruvic Acid | 100 | — | — |
| β-Alanine | Pyruvic Acid | 0 | 100 | — |

TABLE 5-continued

| | | Enzyme | | |
|---|---|---|---|---|
| Amino Group Donor | Amino Group Receptor | A | B | C |
| Taurine | Pyruvic Acid | 0 | 132 | — |
| Putrescine | Pyruvic Acid | 0 | 18 | — |
| β-Alanine | 2-Ketoglutaric Acid | 0 | — | 0 |
| 4-Aminobutyric Acid | 2-Ketoglutaric Acid | 0 | — | 100 |
| Taurine | 2-Ketoglutaric Acid | 0 | — | 8 |

Enzyme A) MTA (present invention)
Enzyme B) ω-Amino Acid: Pyruvic Acid Transaminase (derived from *Pseudomonas* F-126)
Enzyme C) 4-Aminobutylic Acid: 2-Ketoglutaric Acid Transaminase (derived from *Pseudomonas* F-126)

Example 8

Cloning of MTA Gene (Preparation of PCR Primers)

By using protein sequencer ABI 492 (Perkin Elmer Biosystems), an N-terminal amino acid sequence of the purified MTA obtained in Example 1 was determined. Moreover, the purified MTA thus obtained in Example 1 was denatured in the presence of 8M urea and then digested with lysyl endopeptidase derived from *achromobacter* (Wako Pure Chemical Industries Ltd.), thereby obtaining an amino acid sequence cleaved into peptide fragments. The amino acid sequence was determined in the same way as the determination of the N-terminal amino acid sequence. Considering a base sequence predicted from the amino acid sequence, a primer 1 (SEQ ID NO: 3 in the sequence list) and a primer (SEQ ID NO: 4 in the sequence list) for PCR amplification of part of the MTA gene were synthesized.

(PCR Amplification of MTA Gene)

From a culture broth of *Pseudomonas fluorescens* KNK08-18, a genomic DNA was extracted according to a method described by Murray et al. (Nucl. Acids Res., 8, 4321, 1980). PCR was carried out with the genomic DNA as a template, and the primers synthesized above. As a result, a DNA fragment of approximately 540 bp was obtained, which was deduced as part of the MTA gene. The PCR was carried out with TaKaRa Ex Taq (Takara Shuzo Co., Ltd.) as a DNA polymerase, and under reaction conditions as instructed in the manual of TaKaRa Ex Taq. The DNA fragment was cloned with plasmid pT7Blue T-Vector (Novagen). Its base sequence was determined using ABI PRISM Dye Terminator Cycle Sequencing Ready Reaction Kit (Perkin Elmer Inc.) and ABI 310 DNA Sequencer (Perkin Elmer Inc.). The base sequence, labeled as SEQ ID NO: 5, is shown in the sequence list.

(Determination of Whole Sequence of MTA Gene by Inverse-PCR Technique)

The genomic DNA of *Pseudomonas fluorescens* KNK08-18 was completely digested with a restriction enzyme EcoRI, FbaI, NcoI, or SphI. Digestion products thus obtained were intermolecularly cyclized by using T4DNA ligase (Takara Shuzo Co., Ltd.). Using this cyclic compound as a template, the whole base sequence of the MTA gene was determined on the genomic DNA by the inverse-PCR technique (Nucl. Acids Res., 16, 8186 (1988)) referring to the partial base sequence information of the MTA gene determined above. The PCR was carried out with TaKaRa LA Taq with GC buffer (Takara Shuzo Co., Ltd.) under reaction conditions as instructed in the manual of TaKaRa LA Taq with GC buffer. In the sequence list, the base sequence thus determined is shown as SEQ ID NO: 2. The amino acid sequence encoded by the base sequence is shown as SEQ ID NO: 1 in the sequence list.

Example 9

Preparation of Recombinant Plasmid of MTA Gene

Based on the base sequence thus determined in Example 8, a primer 3 (SEQ ID NO: 6) and primer 4 (SEQ ID NO: 7) are synthesized. The primer 3 had NdeI site added at a site corresponding to the initiation condon of the MTA gene. The primer 4 had EcoRI site added at a site right after the termination condon of the MTA gene. PCR was carried out using, as a template, the genomic DNA of *Pseudomonas fluorescens* KNK08-18 obtained in Example 2, and these primers. Thereby, double-strand DNA with NdeI site at the initiation condon of the MTA gene and with EcoRI site right after the termination condon thereof. The PCR was carried out with TaKaRa LA Taq with GC buffer (Takara Shuzo Co., Ltd.) under reaction conditions as instructed in the manual of TaKaRa LA Taq with GC buffer. The DNA was digested with NdeI and EcoRI, and inserted between the NdeI recognizing site and EcoRI recognizing site in the downstream of a lac promoter of a plasmid pUCNT (WO94/03613). Thereby, a recombinant vector pNTMTA was obtained.

Example 10

Preparation of Recombinant *E. coli*

Using the recombinant vector pNTMTA thus obtained in Example 9, *E. coli* HB101 (Takara Shuzo Co., Ltd.) was transformed, thereby obtaining a recombinant *E. coli* HB101 (pNTMTA). On Oct. 5, 2004, the transformant *E. coli* HB101 (pNTMTA) thus obtained was deposited with Accession No. FERM P-20238 at the International Patent Organism Depositiory (IPOD) of the National Institute of Advanced Industrial Science and Technology, whose address is Chuodairoku 1-1-1, Higashi, Tsukuba-shi, Ibaragi Prefecture, Japan (Post Code 305-8566).

Example 11

Expression of the MTA Gene in Recombinant *E. coli*

*E. coli* HB101 (pNTMTA) thus obtained in Example 10 was incubated in 2×YT medium (tryptone 1.6%, yeast extract 1.0%, NaCl 0.5%, pH 7.0) containing ampicillin by 200 μg/ml. Then, incubated cells were collected therefrom, dispersed in a 100 mM phosphate buffer (pH 7.5), and then subjected to ultrasonic disintegration. Thereby, a cell-free extract solution was obtained. The cell-free extract solution was analyzed in transaminase activity by the activity measuring method described in Example 1, using acetophenone and 1-benzyl-3-pyrrolidinone as substrates. In the cell-free extract solution of *E. coli* HB101 (pNTMTA), a transaminase activity of 1 U was observed per 1 mg of protein.

Example 12

Production of Optically Active 7-Methoxy-2-Aminotetralin by Producing Method I

*E. coli* HB101 (pNTMTA) thus obtained in Example 10 was inoculated in 50 mL of 2×YT medium (tryptone 1.6%, yeast extract 1.0%, NaCl 0.5%, ampicillin 200 μg/ml, pH 7.0) in a Sakaguchi flask of 500 mL, and then incubated at 28° C. for 3 days. The cells were collected from the culture broth centrifugally, and dispersed in a 0.01M potassium phosphate buffer (pH 8.0) containing 0.01% 2-mercaptoethanol and 0.02 mM pyridoxal phosphate. The dispersion solution thus prepared was adjusted to a volume of 5 ml, thereby obtaining a cell-dispersion solution.

Into a flask in which substrates, that is, 300 mg of 7-methoxy-2-tetralone and 309.4 mg of (S)-α-phenethylamine were added in advance, 3 ml of the cell-dispersion solution, 3.7 mg of pyridoxal phosphate, and 3 mL of a 1M potassium phosphate buffer (pH 6.8) were introduced. The whole volume was adjusted to 30 mL by adding deionized water therein. This was reacted at 30° C. for 24 hours with stirring. After the reaction is completed, 7-methoxy-2-aminotetralin thus produced in the reaction mixture was analyzed by HPLC with the conditions described below. This showed that 7-methoxy-2-aminotetralin was produced with a conversion rate of 85%, and it had a (S) configuration and optical purity of 96.7% e.e.

[Analysis Conditions of High-Performance Liquid Chromatography]
<Quantitative Analysis>
Column: Cosmosil 5C8-MS (Nacalai Tesque Inc.)
Carrier: 30 mM potassium phosphate buffer (pH 2.5)/acetonitrile/methanol=4/1/1 (by volume)
Flow Rate: 0.9 mL/min
Detection: 254 nm
<Optical Purity Analysis>
Column: Crownpak CR(+) (Daicel Chemical Industries, Ltd.)
Carrier: perchloric acid aqueous solution (pH 1.5)/methanol=85/15 (by volume)
Flow Rate: 0.9 mL/min
Detection: 220 nm
Column Temperature: 47° C.

Example 13

Production of Optically Active 1-benzyl-3-Aminopyrrolidine by Producing Method I In the same manner as in Example 12, a cell-dispersion solution was prepared. Into a flask in which substrates, that is, 900 mg of 1-benzyl-3-pyrrolidinone and 928.2 mg of (S)-α-phenethylamine were added in advance, 3 ml of the cell-dispersion solution, 3.7 mg of pyridoxal phosphate, and 3 mL of a 1M potassium phosphate buffer (pH 6.8) were introduced. The whole volume was adjusted to 30 mL by adding deionized water therein. This was reacted at 30° C. for 16 hours with stirring. After the reaction is completed, 1-benzyl-3-aminopyrrolidine thus produced in the reaction mixture was analyzed via HPLC with the conditions described below. This showed that 1-benzyl-3-aminopyrrolidine was produced with a conversion rate of 75.1%, and it had a (S) configuration and optical purity of 79.2% e.e.

[High-Performance Liquid Chromatography Analysis Conditions]
<Quantitative Analysis>
Column: Finepak SIL C18-T (JASCO Corp.)
Carrier: Distilled Water 1260 mL/Acetonitrile 740 mL/$KH_2PO_4$ 10 g/SDS 2.88 g (pH3.6)
Flow Rate: 1 mL/min
Detection: 254 nm
Column Temperature: 40° C.
<Optical Purity Analysis>
After basified with sodium carbonate of an appropriate amount and derivatized with Z-chloride, the reaction mixture was analyzed with the following conditions.

Column: Chiralcel OD-H (Daicel Chemical Industries, Ltd.)
Carrier: hexane/isopropylalcohol=90/10 (by volume)
Flow Rate: 1.0 mL/min
Detection: 254 nm
Column Temperature: room temperature Example 14

Production of Optically Active 1-Phenyl-3-Butylamine by Producing Method I

In the same manner as in Example 12, a cell-dispersion solution was prepared. Into a flask in which substrates, that is, 504.6 mg of 1-phenyl-3-butanone and 618.8 mg of (S)-α-phenethylamine were added in advance, 3 ml of the cell-dispersion solution, 3.7 mg of pyridoxal phosphate, and 3 mL of a 1M potassium phosphate buffer (pH 6.8) were introduced. The whole volume was adjusted to 30 mL by adding deionized water therein. This was reacted at 30° C. for 16 hours with stirring. After the reaction is completed, 1-phenyl-3-butylamine thus produced in the reaction mixture was analyzed in the manner described below. This showed that 1-phenyl-3-butylamine was produced with a conversion rate of 68%, and it had a (S) configuration and optical purity of 95.8% e.e.

[High-Performance Liquid Chromatography Analysis Conditions]
<Quantitative Analysis>
Column: Cosmosil 5C8-MS (Nacalai Tesque Inc.)
Carrier: 30 mM potassium phosphate buffer (pH 2.5)/acetonitrile/methanol=4/1/1 (by volume)
Flow Rate: 0.9 mL/min
Detection: 254 nm
<Optical Purity Analysis>
After basified with sodium carbonate of an appropriate amount and derivatized with acetic anhydride, the reaction mixture was analyzed with the following conditions.
Column: Chiralcel OJ-H (Daicel Chemical Industries, Ltd.)
Carrier: hexane/ethanol=95/5 (by volume)
Flow Rate: 1.0 mL/min
Detection: 220 nm
Column Temperature: room temperature Example 15

Production of Optically Active 7-Methoxy-2-Aminotetralin by Producing Method II

In the same manner as in Example 12, a cell-dispersion solution was prepared. Into a flask in which substrates, that is, 100 mg of racemic 7-methoxy-2-aminotetralin and 62 mg of pyruvic acid were added in advance, 3 ml of the cell-dispersion solution, 1.2 mg of pyridoxal phosphate, and 1 mL of a 1M potassium phosphate buffer (pH 7.0) were introduced. The whole volume was adjusted to 10 mL by adding deionized water therein. This was reacted at 30° C. for 21 hours with stirring. After the reaction is completed, the reaction mixture was analyzed in the same manner as in Example 12.

This showed that 7-methoxy-2-aminotetralin was produced with a survival rate of 44%, and it had a (R) configuration and optical purity of 100% e.e.

Example 16

Production of Optically Active 2-Aminoheptane by Producing Method I

E. coli HB101 (pNTMTA) thus obtained in Example 10 was inoculated in 50 mL 2×YT medium (tryptone 1.6%, yeast extract 1.0%, NaCl 0.5%, pH 7.0) in a Sakaguchi flask of 500 mL, and then incubated at 28° C. for 3 days. The cells were collected from the culture broth centrifugally, and dispersed in a 0.01M potassium phosphate buffer (pH 8.0) containing 0.01% 2-mercaptoethanol and 0.02 mM pyridoxal phosphate. The dispersion solution thus prepared was adjusted to a volume of 5 ml, thereby obtaining a cell-dispersion solution.

Into a flask in which substrates, that is, 600 mg of 2-heptanone and 955.1 mg of (S)-α-phenethylamine were added in advance, 3 ml of the cell-dispersion solution, 3.7 mg of pyridoxal phosphate, and 3 mL of a 1M potassium phosphate buffer (pH 6.8) were introduced. The whole volume was adjusted to 30 mL by adding deionized water therein. This was reacted at 30° C. for 16 hours with stirring. After the reaction is completed, 2 mL of the reaction mixture was mixed with 200 µL of 40% sodium hydroxide aqueous solution. Then, extraction was carried out with 4 mL of tert-butylmethylether, thereby obtaining an extraction solution, which was then analyzed in the following manner. This showed that 2-aminoheptane was produced with a conversion rate of 47%, and it had a (S) configuration and optical purity of 98.8% e.e.

[Gas Chromatography Analysis Conditions]
<Quantitative Analysis>
Column: Rtx-5 Amine 30 m×0.25 mm (RESTEK Corp.)
Column Temperature: 150° C.
Injector Temperature: 250° C.
Detector Temperature: 250° C.
Carrier Gas: He
Detection: FID
[High-Performance Liquid Chromatography Analysis Conditions]
<Optical Purity Analysis>
After basified with sodium carbonate of an appropriate amount and derivatized with dinitrobenzoyl chloride, the reaction mixture was analyzed with the following conditions.
Column: Chiralpak AD-H (Daicel Chemical Industries, Ltd.)
Carrier: hexane/ethanol=9/1 (by volume)
Flow Rate: 1.0 mL/min
Detection: 240 nm
Column Temperature: 35° C.

Example 17

Production of Optically Active 1-Boc-3-Aminopyrrolidine by Producing Method I

In the same manner as in Example 16, a cell-dispersion solution was prepared. Into a flask in which substrates, that is, 900 mg of 1-Boc-3-pyrrolidinone and 883 mg of (S)-α-phenethylamine were added in advance, 3 ml of the cell-dispersion solution, 3.7 mg of pyridoxal phosphate, and 3 mL of a 1M potassium phosphate buffer (pH 6.8) were introduced. The whole volume was adjusted to 30 mL by adding deionized water therein. This was reacted at 30° C. for 8 hours with stirring. After the reaction is completed, 0.1 mL of the reaction mixture was mixed with 30 µL of 40% sodium hydroxide aqueous solution. Then, extraction was carried out with 1 mL of ethyl acetate, thereby obtaining an extraction solution, which was then analyzed in the following manner. This showed that 1-Boc-3-aminopyrrolidine was produced with a conversion rate of 82%, and it had a (S) configuration and optical purity of 99.4% e.e.

[Gas Chromatography Analysis Conditions]
<Quantitative Analysis>
Column: Rtx-5 Amine 30 m×0.25 mm (RESTEK Corp.)
Column Temperature: 150° C.
Injector Temperature: 250° C.
Detector Temperature: 250° C.
Carrier Gas: He
Detection: FID
[High-Performance Liquid Chromatography Analysis Conditions]
<Optical Purity Analysis>
After basified with sodium carbonate of an appropriate amount and derivatized with dinitrobenzoyl chloride, the reaction mixture was analyzed with the following conditions.
Column: Chiralpak AD-H (Daicel Chemical Industries, Ltd.)
Carrier: hexane/ethanol=75/25 (by volume) with 0.1% diethylamine
Flow Rate: 0.7 mL/min
Detection: 240 nm
Column Temperature: 40° C.

Example 18

Production of Optically Active 1-Boc-3-Aminopiperidine by Producing Method I

In the same manner as in Example 16, a cell-dispersion solution was prepared. Into a flask in which substrates, that is, 900 mg of 1-Boc-3-piperidinone and 821 mg of (S)-α-phenethylamine were added in advance, 3 ml of the cell-dispersion solution, 3.7 mg of pyridoxal phosphate, and 3 mL of a 1M potassium phosphate buffer (pH 6.8) were introduced. The whole volume was adjusted to 30 mL by adding deionized water therein. This was reacted at 30° C. for 5 hours with stirring. After the reaction is completed, 0.2 mL of the reaction mixture was mixed with 50 µL of 40% sodium hydroxide aqueous solution. Then, extraction was carried out with 1 mL of ethyl acetate, thereby obtaining an extraction solution, which was then analyzed in the following manner. This showed that 1-Boc-3-aminopiperidine was produced with a conversion rate of 83%, and it had a (S) configuration and optical purity of >99.9% e.e.

[Gas Chromatography Analysis Conditions]
<Quantitative Analysis>
Column: Rtx-5 Amine 30 m×0.25 mm (RESTEK Corp.)
Column Temperature: 150° C.
Injector Temperature: 250° C.
Detector Temperature: 250° C.
Carrier Gas: He
Detection: FID
[High-Performance Liquid Chromatography Analysis Conditions]
<Optical Purity Analysis>
After basified with sodium carbonate of an appropriate amount and derivatized with dinitrobenzoyl chloride, the reaction mixture was analyzed with the following conditions.

Column: Chiralpak AD-H (Daicel Chemical Industries, Ltd.)
Carrier: hexane/ethanol=75/25 (by volume) with 0.1% diethylamine
Flow Rate: 0.7 mL/min
Detection: 240 nm
Column Temperature: 40° C.

The invention claimed is:

1. An isolated DNA
   (A) having the base sequence of SEQ ID NO: 2 in the sequence list; or
   (B) being hybridizable with DNA complementary with the base sequence of SEQ ID NO: 2 in the sequence list under stringent conditions, and having an amino group transfer activity, which produces acetophenone and 1-benzyl-3-aminopyrrolidine from 1-benzyl-3-pyrrolidinone and optically active (S)-α-phenethylamine,
   wherein said DNA encodes an aminotransferase enzyme, and
   wherein the stringent conditions are conditions in which hybridization is carried out at 65° C. in the presence of NaCl of 0.7 M to 1.0 M with a filter on which a polynucleotide derived from a colony or plaque is immobilized, and then the filter is washed at 65° C. with a 2×SSC solution.

2. A vector having DNA as set forth in claim 1.

3. A transformant obtained by transformation of a host cell with a vector as set forth in claim 2.

4. An isolated DNA encoding an aminotransferase having physical and chemical properties (1) to (6):
   (1) effect: the aminotransferase catalyzes an amino group transfer reaction that produces acetophenone and 1-benzyl-3-aminopyrrolidine from 1-benzyl-3-pyrrolidinone and optically active (S)-α-phenethylamine;
   (2) substrate specificities:
      (a) amino donor: the aminotransferase is active with (S)-α-phenethylamine, but substantially inactive with β-alanine, taurine, putrescine, DL-ornithine, and DL-lysine; and
      (b) amino acceptor: the aminotransferase is active with pyruvic acid and glyoxylic acid;
   (3) molecular weight: approximately 120,000 when measured by gel filtration, and approximately 53,000 when measured by SDS-polyacrylamide gel electrophoresis;
   (4) an optimum pH of 7 to 9;
   (5) an optimum temperature for activity of 30° C. to 50° C.; and
   (6) a thermal stability after being treated with a pH of 7.0 and a temperature of 30° C. to 40° C. for 30 minutes, and wherein the enzyme maintains 90% or more of its activity that the enzyme had before treatment.

5. A vector having DNA as set forth in claim 4.

6. A transformant obtained by transformation of a host cell with a vector as set forth in claim 5.

7. The isolated DNA according to claim 1, wherein said DNA encodes an aminotransferase comprising SEQ ID NO: 1.

8. The vector having DNA according to claim 2, wherein said DNA encodes an aminotransferase comprising SEQ ID NO: 1.

9. The transformant according to claim 3, wherein said DNA encodes an aminotransferase comprising SEQ ID NO: 1.

10. The isolated DNA according to claim 1, wherein said DNA comprises the polynucleotide sequence of SEQ ID NO: 2.

11. The vector having DNA according to claim 2, wherein said DNA comprises the polynucleotide sequence of SEQ ID NO: 2.

12. The transformant according to claim 3, wherein said DNA comprises the polynucleotide sequence of SEQ ID NO: 2.

* * * * *

SEQUENCE LISTING

<160> NUMBER OF SEQ ID NOS: 7

<210> SEQ ID NO 1
<211> LENGTH: 454
<212> TYPE: PRT
<213> ORGANISM: Pseudomonas fluorescens

<400> SEQUENCE: 1

```
Met Asn Ser Asn Asn Lys Ala Trp Leu Lys Glu His Asn Thr Val His
 1               5                  10                  15

Met Met His Pro Met Gln Asp Pro Lys Ala Leu His Glu Gln Arg Pro
            20                  25                  30

Leu Ile Ile Gln Ser Gly Lys Gly Val His Ile Thr Asp Val Asp Gly
        35                  40                  45

Arg Arg Phe Ile Asp Cys Gln Gly Gly Leu Trp Cys Val Asn Ala Gly
    50                  55                  60

Tyr Gly Arg Arg Glu Ile Ile Asp Ala Val Thr Arg Gln Met Glu Glu
65                  70                  75                  80

Leu Ala Tyr Tyr Ser Leu Phe Pro Gly Ser Thr Asn Ala Pro Ala Ile
                85                  90                  95

Ala Leu Ser Gln Lys Leu Thr Glu Val Ala Ala Glu Glu Gly Met Val
            100                 105                 110

Lys Ala Ser Phe Gly Leu Gly Gly Ser Asp Ala Val Glu Thr Ala Leu
        115                 120                 125

Lys Ile Ala Arg Gln Tyr Trp Lys Leu Glu Gly Gln Pro Asp Lys Val
    130                 135                 140

Lys Phe Val Ser Leu Tyr Asn Gly Tyr His Gly Leu Asn Phe Gly Gly
145                 150                 155                 160

Met Ser Ala Cys Gly Gly Asn Ala Trp Lys Ser Ser Tyr Glu Pro Leu
                165                 170                 175

Met Pro Gly Phe Phe Gln Val Glu Ser Pro His Leu Tyr Arg Asn Pro
            180                 185                 190

Phe Thr Asn Asp Pro Glu Glu Leu Ala Glu Ile Cys Ala Gln Ile Leu
        195                 200                 205

Glu Arg Gln Ile Glu Met Gln Ala Pro Gly Thr Val Ala Ala Leu Ile
    210                 215                 220

Ala Glu Pro Ile Gln Gly Ala Gly Gly Val Ile Val Pro Pro Ala Ser
225                 230                 235                 240

Tyr Trp Pro Arg Leu Arg Gln Ile Cys Asp Lys Tyr Asp Ile Leu Leu
                245                 250                 255

Ile Ala Asp Glu Val Ile Thr Gly Leu Gly Arg Ser Gly Ser Leu Phe
            260                 265                 270

Gly Ser Arg Gly Trp Gly Val Lys Pro Asp Ile Met Cys Leu Ala Lys
        275                 280                 285

Gly Ile Ser Ser Gly Tyr Val Pro Leu Ser Ala Thr Leu Val Asn Ser
    290                 295                 300

Arg Val Ala Arg Ala Trp Glu Arg Asp Ala Gly Phe Thr Ser Val Tyr
305                 310                 315                 320

Met His Gly Tyr Thr Tyr Ser Gly His Pro Val Ser Cys Ala Ala Ala
                325                 330                 335
```

```
Leu Ala Ala Ile Asp Ile Val Leu Gln Glu Asn Leu Ala Glu Asn Ala
            340                 345                 350

Arg Val Val Gly Asp Tyr Phe Leu Glu Lys Leu Leu Ile Leu Lys Asp
            355                 360                 365

Lys His Arg Ala Ile Gly Asp Val Arg Gly Lys Gly Leu Met Leu Ala
            370                 375                 380

Val Glu Leu Val Lys Glu Arg Ala Thr Lys Glu Pro Phe Gly Pro Ala
385                 390                 395                 400

Asp Ala Tyr Pro Leu Ala Ile Ser Glu Ala Cys Val Asn Asn Gly Val
            405                 410                 415

Met Ile Arg Thr Ile Val Asn Lys Leu Ile Ile Ser Pro Pro Leu Thr
            420                 425                 430

Phe Thr Thr Glu His Val Asp Glu Val Ile Glu Val Leu Asp Arg Ala
            435                 440                 445

Phe Val Ala Asn Pro Trp
            450

<210> SEQ ID NO 2
<211> LENGTH: 1365
<212> TYPE: DNA
<213> ORGANISM: Pseudomonas fluorescens

<400> SEQUENCE: 2
atgaacagca acaacaaagc ctggctcaaa gagcacaaca cggtgcacat gatgcatccg      60
atgcaggatc cgaaagcact gcacgaacag cgcccattga ttattcagtc cggtaagggc     120
gtacacatca ctgatgttga cgggcgtcgc ttcatcgatt gccagggcgg actatggtgc     180
gtcaatgccg gttacggtcg acgtgaaatc atcgacgcgg tgacccggca gatgaaagag     240
ctggcgtact attcgttgtt tcccggcagc accaatgcgc cggccattgc gctttcgcag     300
aagttgaccg aggtggcggc cgaggagggc atggtcaagg catcgtttgg tctcggcggt     360
tcggacgccg tggagactgc gctgaaaatc gctcgtcaat actggaagct ggaaggccag     420
cccgacaagg tcaagttcgt ctcgtttgtac aacggctatc acggcctgaa cttcggtggc     480
atgtccgcct gtggcggcaa cgcctggaaa agcagctacg aacccttgat gccgggcttc     540
ttccaggtcg aatcaccgca tctataccgc aaccctttca ccaatgatcc agaggaactc     600
gcagaaatct gtgcgcagat cctgagcgg caaatcgaaa tgcaagcgcc gggcactgtc     660
gcggcgttga ttgccgagcc gatccaggga gctggcggag tcatcgtacc ccagcctct     720 tattggccgc gcttgcgcca gatctgcgac aagtatgaca ttctactgat cgccgatgag     780
gtcatcaccg actgggtcg cagcggttcg ttgttcggtt cccgtggttg gggggtcaag     840
cccgacatca tgtgcctggc aaaggtatc agcagcggtt atgtgcctct gagcgcgaca     900
ctggtcaact cccgcgtcgc ccgggcatgg gagcgtgatg ccggtttcac ctcggtctac     960
atgcatggct acacctattc cggtcaccct gtctcttgcg ccgctgcgct ggcggccatc    1020
gacatcgtgc tgcaggagaa tctcgccgaa acgcacgggg tggttggcga ctatttcctg    1080
gagaagctgc tgatactcaa ggacaaacat cgggccatcg gcgatgtgcg cggcaagggg    1140
ctgatgctgg cagtcgagct ggtcaaggaa agggcgacca aggagccgtt cggcccggca    1200
gacgcttatc cgctggccat ttccgaggcc tgtgtgaata cggagtgat gattcgtacc    1260 atcgtcaaca agctgatcat ctcgccgccg ttgaccttca ccaccgagca tgtcgacgaa    1320
gtgatcgagg tgctcgaccg cgccttcgtt gccaaccct ggtaa                    1365
```

```
<210> SEQ ID NO 3
<211> LENGTH: 20
<212> TYPE: DNA
<213> ORGANISM: Artificial Sequence
<220> FEATURE:
<223> OTHER INFORMATION: Synthetic primer 1
<220> FEATURE:
<221> NAME/KEY: misc_feature
<222> LOCATION: (6)..(6)
<223> OTHER INFORMATION: n represents a, t, g or c
<220> FEATURE:
<221> NAME/KEY: misc_feature
<222> LOCATION: (9)..(9)
<223> OTHER INFORMATION: n represents a, t, g or c

<400> SEQUENCE: 3
aayacngtnc ayatgatgca                                                20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer 2
<220> FEATURE:
<221> NAME/KEY: misc_feature
<222> LOCATION: (12)..(12)
<223> OTHER INFORMATION: n represents a, t, g or c
<220> FEATURE:
<221> NAME/KEY: misc_feature
<222> LOCATION: (15)..(15)
<223> OTHER INFORMATION: n represents a, t, g or c

<400> SEQUENCE: 4
acytgraara anccnggcat                                                20

<210> SEQ ID NO 5
<211> LENGTH: 472
<212> TYPE: DNA
<213> ORGANISM: Pseudomonas fluorescens

<400> SEQUENCE: 5
atccgatgca ggatccgaaa gcactgcacg aacagcgccc attgattatt cagtccggta    60
agggcgtaca catcactgat gttgacgggc gtcgcttcat cgattgccag ggcggactat   120
ggtgcgtcaa tgccggttac ggtcgacgtg aaatcatcga cgcggtgacc cggcagatgg   180
aagagctggc gtactattcg ttgtttcccg gcagcaccaa tgcgccggcc attgcgcttt   240
cgcagaagtt gaccgaggtg gcggccgagg agggcatggt caaggcatcg tttggtctcg   300
gcggttcgga cgccgtggag actgcgctga aaatcgctcg tcaatactgg aagctggaag   360
gccagcccga caaggtcaag ttcgtctcgt tgtacaacgg ctatcacggc ctgaacttcg   420
gtggcatgtc cgcctgtggc ggcaacgcct ggaaaagcag ctacgaaccc tt           472

<210> SEQ ID NO 6
<211> LENGTH: 33
<212> TYPE: DNA
<213> ORGANISM: Artificial Sequence
<220> FEATURE:
<223> OTHER INFORMATION: Synthetic primer 3

<400> SEQUENCE: 6
tggagtggcc atatgaacag ccaacaacaa agc                                 33

<210> SEQ ID NO 7
<211> LENGTH: 33
<212> TYPE: DNA
<213> ORGANISM: Artificial Sequence
```

```
<220> FEATURE:
<223> OTHER INFORMATION: Synthetic primer 4

<400> SEQUENCE: 7
tggtcagcga attcttacca ggggttggca acg                                33
```